(12) United States Patent
Ueno

(10) Patent No.: US 8,143,316 B2
(45) Date of Patent: Mar. 27, 2012

(54) METHOD FOR TREATING PERIPHERAL VASCULAR DISEASES

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 632 days.

(21) Appl. No.: 11/366,413

(22) Filed: Mar. 3, 2006

(65) Prior Publication Data

US 2006/0247317 A1 Nov. 2, 2006

Related U.S. Application Data

(60) Provisional application No. 60/658,144, filed on Mar. 4, 2005.

(51) Int. Cl.
- *A01N 35/00* (2006.01)
- *A01N 31/00* (2006.01)
- *A61K 31/12* (2006.01)
- *A61K 31/045* (2006.01)

(52) U.S. Cl. .................. 514/690; 514/729; 514/675

(58) Field of Classification Search ............ 514/183
See application file for complete search history.

(56) References Cited

U.S. PATENT DOCUMENTS

| | | | |
|---|---|---|---|
| 3,671,570 A | 6/1972 | Bagli et al. | |
| 4,119,727 A | 10/1978 | Buendia et al. | |
| 4,126,754 A | 11/1978 | Bundy et al. | |
| 4,138,577 A * | 2/1979 | Bundy et al. | 560/55 |
| 4,254,145 A * | 3/1981 | Birnbaum | 514/530 |
| 5,001,153 A | 3/1991 | Ueno et al. | |
| 5,212,324 A | 5/1993 | Ueno | |
| 5,225,439 A | 7/1993 | Ueno et al. | |
| 5,252,605 A | 10/1993 | Ueno | |
| 5,254,588 A | 10/1993 | Ueno et al. | |
| 5,256,696 A | 10/1993 | Ueno et al. | |
| 5,317,032 A | 5/1994 | Ueno et al. | |
| 5,346,921 A | 9/1994 | Ueno | |
| 5,773,471 A | 6/1998 | Oguchi et al. | |
| 6,197,821 B1 | 3/2001 | Ueno | |
| 6,291,521 B1 | 9/2001 | Ueno | |
| 6,414,016 B1 | 7/2002 | Ueno | |
| 6,566,398 B1 | 5/2003 | Ueno | |
| 2003/0171438 A1* | 9/2003 | Ueno | 514/573 |

FOREIGN PATENT DOCUMENTS

| | | |
|---|---|---|
| DE | 28 03 127 A1 | 7/1979 |
| EP | 0 690 049 A2 | 1/1996 |
| GB | 1 292 661 | 10/1972 |
| WO | WO 01/05388 A2 | 1/2001 |

OTHER PUBLICATIONS

Tooke J. E.; Peripheral Microvascular Disease in Diabetes; Diabetes Research and Clinical Practice; vol. 30 Suppl, Feb. 1996, pp. S61-S65.

* cited by examiner

*Primary Examiner* — Jeffrey S. Lundgren
*Assistant Examiner* — Meghan Finn
(74) *Attorney, Agent, or Firm* — Sughrue Mion, PLLC

(57) ABSTRACT

The present invention provides a method for treating peripheral vascular diseases in a mammalian subject, which comprises administering to the patient in need thereof an effective amount of 11-deoxy-prostaglandin compound.

50 Claims, 21 Drawing Sheets

METHOD FOR TREATING PERIPHERAL VASCULAR DISEASES

CROSS-REFERENCE TO RELATED APPLICATION

The Applicant claims the benefit of U.S. Provisional Application No. 60/658,144 filed Mar. 4, 2005.

TECHNICAL FIELD

The present invention relates to a method for treating peripheral vascular diseases in a mammalian subject using a specific prostaglandin compound. The invention also relates to a composition which is useful for the method.

BACKGROUND ART

Vascular diseases are often the result of decreased perfusion in the vascular system or physical or biochemical injury to the blood vessel.

Peripheral vascular disease (PVD) is defined as a disease of blood vessels often encountered as narrowing of the vessels of the limbs. There are two main types of these disorders, functional disease which doesn't involve defects in the blood vessels but rather arises from stimuli such as cold, stress, or smoking, and organic disease which arises from structural defects in the vasculature such as atherosclerotic lesions, local inflammation, or traumatic injury. This can lead to occlusion of the vessel, aberrant blood flow, and ultimately to tissue ischemia.

One of the more clinically significant forms of PVD is peripheral artery disease (PAD). PAD is often treated by angioplasty and implantation of a stent or by artery by-pass surgery. Clinical presentation depends on the location of the occluded vessel. For example, narrowing of the artery that supplies blood to the intestine can result in severe postprandial pain in the lower abdomen resulting from the inability of the occluded vessel to meet the increased oxygen demand arising from digestive and absorptive processes. Severe forms the ischemia can lead to intestinal necrosis. Similarly, PAD in the leg can lead to intermittent pain, usually in the calf, that comes and goes with activity. This disorder is known as intermittent claudication (IC) and can progress to persistent pain while resting, ischemic ulceration, and even amputation.

Peripheral vascular disease is also manifested in atherosclerotic stenosis of the renal artery, which can lead to renal ischemia and kidney dysfunction.

One disease in which vascular diseases and their complications are very common is diabetes mellitus.

Diabetes mellitus causes a variety of physiological and anatomical irregularities, the most prominent of which is the inability of the body to utilize glucose normally, which results in hyperglycemia. Chronic diabetes can lead to complications of the vascular system which include atherosclerosis, abnormalities involving large and medium size blood vessels (macroangiopathy) and abnormalities involving small blood vessels (microangiopathy) such as arterioles and capillaries.

Patients with diabetes mellitus are at increased risk of developing one or more foot ulcers as a result of established long-term complications of the disease, which include impaired nerve function (neuropathy) and/or ischemia.

Local tissue ischemia is a key contributing factor to diabetic foot ulceration. In addition to large vessel disease, patients with diabetes suffer further threat to their skin perfusion in at least two additional ways. First, by involvement of the non-conduit arteries, which are detrimentally affected by the process of atherosclerosis. Second, and perhaps more importantly, by impairment of the microcirculatory control mechanisms (small vessel disease). Normally, when a body part suffers some form of trauma, the body part will, as part of the body's healing mechanism, experience an increased blood flow. When small vessel disease and ischemia are present, as in the case of many diabetics, this natural increased blood flow response is significantly reduced. This fact, together with the tendency of diabetics to form blood clots (thrombosis) in the microcirculatory system during low levels of blood flow, is believed to be an important factor in ulcer pathogenesis.

Neuropathy is a general term which describes a disease process which leads to the dysfunction of the nervous system, and one of the major complications of diabetes mellitus, with no well-established therapies for either its symptomatic treatment or for prevention of progressive decline in nerve function.

The thickening and leakage of capillaries caused by diabetes primarily affect the eyes (retinopathy) and kidneys (nephropathy). The thickening and leakage of capillaries caused by diabetes are also associated with skin disorders and disorders of the nervous system (neuropathy). The eye diseases associated with diabetes are nonproliferative diabetic retinopathy, proliferative diabetic retinopathy, diabetic maculopathy, glaucoma, cataracts and the like.

Others, although not known to be related to diabetes are similar in their physiological effects on the peripheral vascular system. Such diseases include Raynaud syndrome, CREST syndrome, autoimmune diseases such as erythematosis, rheumatoid disease, and the like.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

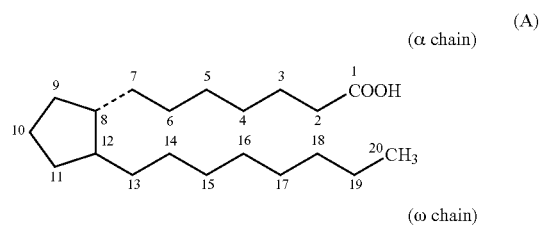

On the other hand, some of synthetic analogues of primary PGs have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

$PGE_1$ and $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and PGF$_{3\alpha}$ have been known to have hypertension, vasoconstriction, intestinal tract movement enhancement, uterine contraction, lutein body atrophy and bronchoconstriction activities.

Some 15-keto (i.e., having oxo at the 15-position instead of hydroxy)-PGs and 13,14-dihydro (i.e., having single bond between the 13 and 14-position)-15-keto-PGs are known as the substances naturally produced by the action of enzymes during the metabolism of primary PGs.

U.S. Pat. No. 6,197,821 to Ueno et al. describes that some 15-keto-PGE compounds are an antagonist for endothelin which is considered to have a relation to hypertension, Buerger disease, asthma, eyegrounds diseases, and the like (the cited reference is herein incorporated by reference).

U.S. Pat. No. 6,197,821 indicates that when the bond between 13- and 14-positions is saturated, a keto-hemiacetal equilibrium may sometimes be formed by the formation of a hemiacetal between the hydroxy group at 11-position and the keto group at 15-position (the cited reference is herein incorporated by reference).

U.S. Pat. No. 5,317,032 to Ueno et al. describes prostaglandin compound cathartics, including the existence of bicyclic tautomers and U.S. Pat. No. 6,414,016 to Ueno describes the bicyclic tautomers as having pronounced activity as anti-constipation agents (the cited references are herein incorporated by reference). The bicyclic tautomers, substituted by one or more halogen atoms can be employed in small doses for relieving constipation. At the C-16 position, especially, fluorine atoms can be employed in small doses for relieving constipation.

Currently used oral drugs for peripheral vascular diseases include cilostazol (commercial name: Pletaal) and prostaglandin (PG) preparations (commercial names: Dorner, Opalmon, etc.) having a vasodilative effect as well as an antiplatelet effect, ticlopidine mainly having an antiplatelet effect (commercial name: Panaldine), sarpogrelate (commercial name: Anplag) and ethyl icosapentate (commercial name: Epadel) which is also adaptable to hyperlipemia. They have different action mechanisms, so that it may be required to use two or three preparations in combination depending on pathology. Particularly in medium illness, multiple drugs are more likely to be applied. Injectable preparations include prostaglandin E1 preparations, antithrombin preparations (commercial name: Argatroban). They are in principle used for medium or more severe illness requiring hospitalization.

The efficacy of the existing drugs is not wholly satisfactory. Particularly, antiplatelets such as ticlopidine or ethyl icosapentate are less effective, probably because it is unclear to which extent platelets are involved in each pathology, or whether the vasodilative effect is sufficient even if a drug has such an effect, or whether bloodstream at ischemic sites can be selectively enough ensured.

SUMMARY OF THE INVENTION

The present inventor conducted an intensive study and found that 11-deoxy-prostaglandin compounds possessed selective significant effects on the peripheral vascular diseases, which resulted in the completion of the present invention.

Namely, the present invention relates to a method for treating a peripheral vascular disease in a mammalian subject, which comprises administering an effective amount of a 11-deoxy-prostaglandin compound to the subject in need thereof.

The present invention further relates to a composition for treating a peripheral vascular disease in a mammalian subject, which comprises an effective amount of a 11-deoxy-prostaglandin compound.

Furthermore, the present invention relates to use of a 11-deoxy-prostaglandin compound for manufacturing a composition for treating a peripheral vascular disease in a mammalian subject, wherein the composition comprises an effective amount of a 11-deoxy-prostaglandin compound.

Another embodiment of the present invention relates to a method for treating damaged peripheral vascular wall and/or peripheral vascular endothelial cells in a mammalian subject, which comprises administering an effective amount of a 11-deoxy-prostaglandin compound to the subject in need thereof.

DETAILED DESCRIPTION OF THE INVENTION

Figure 1A:
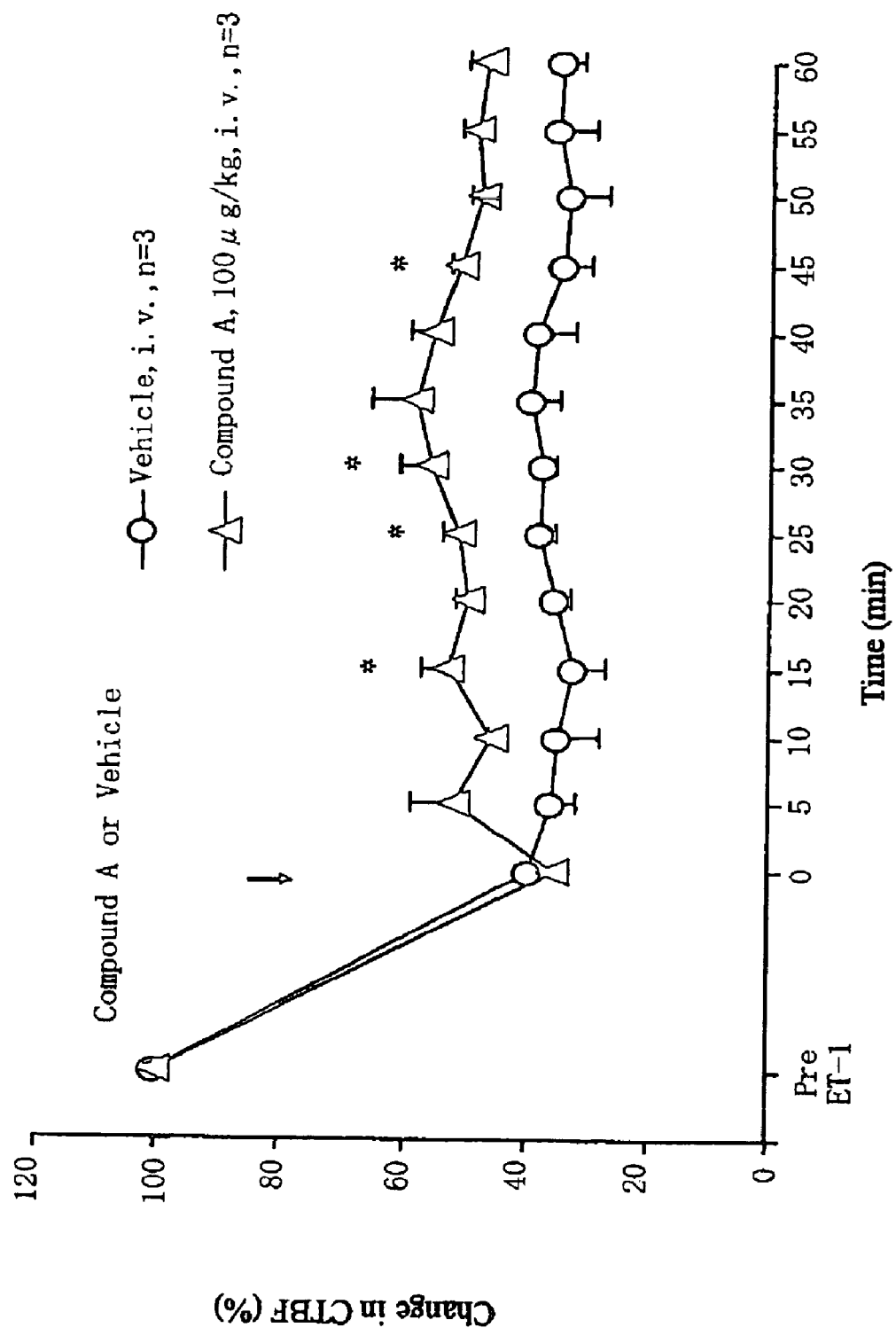
FIG. 1A is a graph showing the effect of Compound A (11-deoxy-13,14-dihydro-15-keto-16,16-difluoro-PGE$_1$) on the decreased peripheral microcirculation in rats induced by ET-1. In the graph, data are presented as mean±S.E., *p<0.05 compared with the vehicle-treated control. CTBF: cutaneous tissue blood flow.

In the present invention, the "11-deoxy-prostaglandin compound" (hereinafter, referred to as "11-deoxy-PG compound") may include any of derivatives or analogs (including substituted derivatives) of a compound having no substituent at 11-position of the prostanoic acid skeleton, irrespective of the configuration of the five-membered ring, the number of double bonds, presence or absence of a substituent, or any other modification in the α or ω chain.

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1); and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

As stated above, the nomenclature of the 11-deoxy-PG compounds is based on the prostanoic acid skeleton. However, in case the compound has a similar partial structure as a prostaglandin, the abbreviation of "PG" may be used. Thus, a 11-deoxy-PG compound of which α-chain is extended by two carbon atoms, that is, having 9 carbon atoms in the α-chain is named as 2-decarboxy-2-(2-carboxyethyl)-11-deoxy-PG compound. Similarly, 11-deoxy-PG compound having 11 carbon atoms in the α-chain is named as 2-decarboxy-2-(4-carboxybutyl)-11-deoxy-PG compound. Further, 11-deoxy-PG compound of which ω-chain is extended by two carbon atoms, that is, having 10 carbon atoms in the ω-chain is named as 11-deoxy-20-ethyl-PG compound. These compounds, however, may also be named according to the IUPAC nomenclatures.

Examples of the analogs (including substituted derivatives) or derivatives include a 11-deoxy-PG compound of which carboxy group at the end of α-chain is esterified; a compound of which α-chain is extended; physiologically acceptable salt thereof; a Compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

The nomenclature of the 11-deoxy-PG compounds used herein is based on the numbering system of the prostanoic acid represented in the above formula (A).

A preferred compound used in the present invention is represented by the formula (I):

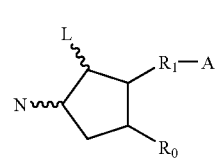

(I)

wherein L and N are hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R$_0$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, and at least one of carbon atom in the aliphatic hydrocarbon is optionally substituted by oxygen, nitrogen or sulfur.

A more preferred compound used in the present invention is represented by the formula (II):

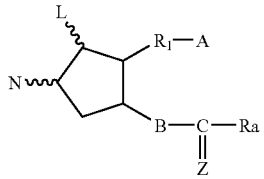
(II)

wherein L and N are hydrogen, hydroxy, halogen, lower alkyl, hydroxy(lower)alkyl, lower alkanoyloxy or oxo, wherein the five-membered ring may optionally have at least one double bond;

A is —CH$_3$, —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

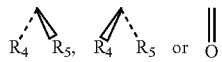

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, and at least one of carbon atom in the aliphatic hydrocarbon is optionally substituted by oxygen, nitrogen or sulfur.

A group of particularly preferable compounds among the above-described compounds is represented by the formula (III):

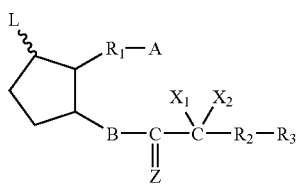
(III)

wherein L is hydrogen, hydroxy, halogen, lower alkyl, hydroxy(lower)alkyl, lower alkanoyloxy or oxo, wherein, and the five-membered ring may optionally have at least one double bond;

A is —CH$_3$, —CH$_2$OH, —COCH$_2$OH, —COOH or a functional derivative thereof;

B is single bond; —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

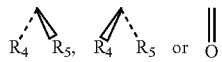

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R$_2$ is a single bond or lower alkylene; and R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for R$_1$ and 1 to 10, especially 1 to 8 carbon atoms for R$_a$.

The term "halogen" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester, The amide of A mean a group represented by the formula —CONR'R", wherein each of R' and R" is hydrogen atom, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L include hydroxy or oxo which has a 5-membered ring structure of, so called, especially PGF or PGE type.

Preferred example A is —COOH, its pharmaceutically acceptable salt, ester or amide thereof.

Preferred example B is —$CH_2$—$CH_2$—, which provide the structure of so-called, 13,14-dihydro type.

Preferred example of $X_1$ and $X_2$ is hydrogen, or that at least one of them is halogen, more preferably, both of them are halogen, especially, fluorine that provides a structure of, so called 16,16-difluoro type.

Preferred $R_1$ is a hydrocarbon containing 1-10 carbon atoms, preferably, 6-10 carbon atoms. Further, at least one of carbon atom in the aliphatic hydrocarbon is optionally substituted by oxygen, nitrogen or sulfur.

Examples of $R_1$ include, for example, the following groups:

—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—CH($CH_3$)—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—,
—$CH_2$—$CH_2$—$CH_2$—$CH_2$—$CH_2$—$CH_2$—CH($CH_3$)—$CH_2$—

Preferred Ra is a hydrocarbon containing 1-10 carbon atoms, more preferably, 1-8 carbon atoms. Ra may have one or two side chains having one carbon atom.

Preferred $R_2$ is single bond, and preferred $R_3$ is lower alkyl. $R_3$ may have one or two side chains having one carbon atom.

The configuration of the ring and the α- and/or ω chains in the above formulae (I), (II) and (III) may be the same as or different from that of the primary PGs. However, the present invention also includes a mixture of a compound having a primary type configuration and a compound of a non-primary type configuration.

The typical example of the present compound is a 11-deoxy-13,14-dihydro-16,16-difluoro-PGE or PGF compound, 11-deoxy-13,14-dihydro-15-keto-16,16-difluoro-PGE or PGF compound, 2-decarboxy-2-(2-carboxyethyl)-11-deoxy-13,14-dihydro-15-keto-16,16-difluoro-PGE or PGF compound, or 11-deoxy-13,14-dihydro-15-keto-16,16-difluoro-20-ethyl-PGE or PGF compound and its derivative or analogue. The preferable example of the present compound is a 11-deoxy-13,14-dihydro-15-keto-16,16-difluoro-$PGE_1$, 11-deoxy-13,14-dihydro-16,16-difluoro-$PGE_1$, 11-deoxy-13,14-dihydro-15-keto-16,16-difluoro-$PGE_1$ isopropyl ester, 2-decarboxy-2-(2-carboxyethyl)-11-deoxy-13,14-dihydro-15-keto-16,16-difluoro-$PGE_1$ isopropyl ester, 2-decarboxy-2-(2-carboxyethyl)-11-deoxy-13,14-dihydro-15-keto-16,16-difluoro-$PGE_1$, 11-deoxy-13,14-dihydro-15-keto-16,16-difluoro-20-methyl-$PGE_1$ isopropyl ester, 11-deoxy-13,14-dihydro-15-keto-16,16-difluoro-20-methyl-$PGE_1$, 11-deoxy-13,14-dihydro-15-keto-16,16-difluoro-20-ethyl-$PGE_1$, 11-deoxy-13,14-dihydro-15-keto-16,16-difluoro-$PGE_1$ methyl ester, 11-deoxy-13,14-dihydro-15-keto-16,16-difluoro-20-ethyl-$PGE_1$ isopropyl ester or 11-deoxy-13,14-dihydro-15-keto-16,16-difluoro-$PGF_{1\alpha}$ isopropyl ester.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324 and 5,739,161 and 6,242,485 (these cited references are herein incorporated by reference).

According to the present invention, a mammalian subject may be treated by the instant invention by administering the above described compound. The subject may be any mammalian subject including a human. The compound can be applied systemically or topically. Usually, the compound may be administered by oral administration, intranasal administration, inhalational administration, intravenous injection (including infusion), subcutaneous injection, intra rectal administration, intra vaginal administration, transdermal administration, eye local administration (e.g. periocular (e.g., subTenon's), subconjunctival, intraocular, intravitreal, intracameral, subretinal, suprachoroidal, and retrobulbar administrations) and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.000001-500 mg/kg, more preferably 0.00001-100 mg/kg per day.

The compound may preferably be formulated in a pharmaceutical composition suitable for administration in a conventional manner. The composition may be those suitable for oral administration, injection or perfusion as well as it may be an external agent, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary.

They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. Purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of injectable compositions of the present invention for parenteral administration include sterile aqueous or non-aqueous solutions, suspensions and emulsions.

Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization.

The injectable composition may also be provided as a sterilized powder composition to be dissolved in a sterilized solvent for injection before use.

Examples of external agent include all the external preparations used in the fields of dermatology and otolaryngology, which includes ointment, cream, lotion and spray.

The present compound is also applied by means of ophthalmic solution, eye drop, eye ointment and the like. The form includes all the formulations for eye local administration used in the ophthalmic field.

The ophthalmic solution or eye drops are prepared by dissolving active ingredients in a sterile aqueous solution such as saline and buffering solution, or by combining powder compositions to be dissolved before use. The eye ointments are prepared by mixing the active ingredient into the base. The formulations may be prepared according to any of the conventional methods.

Osmolarity modifiers may be any of those ordinarily used in the ophthalmic field. Examples of osmolarity modifiers include, but not limited thereto, sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, boric acid, borax, sodium hydroxide, hydrochloric acid, mannitol, isosorbitol, propylene glycol, glucose and glycerineas.

Further, additives ordinarily used in the ophthalmic field may be added to the present composition as desired. Such additives include, for example, buffer agent (e.g., boric acid, sodium monohydrogen phosphate and sodium dihydrogen phosphate), preservatives (e.g., benzalkonium chloride, benzethonium chloride and chlorobutanol), thickeners (e.g., saccharide, such as lactose and mannitol, maltose; e.g., hyaluronic acid or its salt such as sodium hyaluronate and potassium hyaluronate; e.g., mucopolysaccharide such as chondroitin sulfate; e.g., sodium polyacrylate, carboxyvinyl polymer and crosslinked polyacrylate), all of which are included herein by reference.

In preparing the present composition as an eye ointment, other than the above additives, the composition may contain ordinarily used eye ointment base. Such eye ointment base includes, but not limited to, oil base such as vaseline, liquid paraffin, polyethylene, selen 50, plastibase, macrogol or a combination thereof; emulsion base having oil phase and water phase emulsified with surfactant; and water soluble base such as hydroxypropylmethylcellulose, carboxypropylmethylcellulose, and polyethylene glycol.

The present composition may be formulated as a sterile unit dose type containing no preservatives.

Another form of the present invention is suppository or pessary, which may be prepared by mixing active ingredients into a conventional base such as cacao butter that softens at body temperature, and nonionic surfactants having suitable softening temperatures may be used to improve absorbability.

The term "treatment" used herein includes any means of control of the disease or condition, such as prevention, care, relief of the condition, attenuation of the condition and arrest of progression.

The compounds used in the present invention have a significant effect on recovery of the insufficient peripheral circulation, damaged peripheral vascular wall and/or peripheral vascular endothelial cells.

Accordingly, the compounds are useful for treating peripheral vascular diseases, especially peripheral vascular and microvascular diseases. Peripheral vascular and microvascular diseases in this specification and claims may include diseases of the retina, skin, general circulation, kidney, or peripheral or autonomic nervous system. All of these diseases are often associated with diabetes mellitus, and may occur as symptoms associated with the acute or chronic complications of diabetes mellitus. In addition, other diseases, although not known to be related to diabetes, are similar in their physiological effects on the peripheral vascular system and such diseases are also effectively treated by the method of the present invention.

The present invention would also be beneficial in peripheral and autonomic neuropathies or any other diseases that result from a small vessel disease and directly large vessel disease. The beneficial effect of the method is believed to be due to increase of the small vessel blood flow and protection of the vascular endothelial cells.

The term "peripheral vascular diseases" used herein comprise any peripheral vascular disease including peripheral and autonomic neuropathies. Examples of "peripheral vascular disease" include peripheral arterial disease, such as chronic arterial occlusion including arteriosclerosis, arteriosclerosis obliterans and thromboangiitis obliterans (Buerger's disease), macroangiopathy, microangiopathy, diabetes mellitus, thrombophlebitis, phlebemphraxis, Raynaud's disease, Raynaud's syndrome, CREST syndrome, Health hazard due to vibration, Sudeck's syndrome, Intermittent claudication, Cold sense in extremities, Abnormal sensation in extremities, sensitivity to the cold, Meniere's disease, Meniere's syndrome, numbness, lack of sensation, anesthesia, resting pain, causalgia(burning pain), disturbance of peripheral circulation function, disturbance of nerve function, disturbance of motor function, motor paralysis, diabetic peripheral circulation disorder, lumbar spinal canal stenosis, diabetic neuropathy, shock, autoimmune disease such as erythematosis, rheumatoid disease and rheumatoid arthritis, autonomic neuropathy, diabetic autonomic neuropathy, autonomic imbalance, orthostatic hypotension, erectile dysfunction, female sexual dysfunction, retrograde ejaculation, cystopathy, neurogenic bladder, defective vaginal lubrication, exercise intolerance, cardiac denervation, heat intolerance, gustatory sweating, diabetic complication, hyperglycemia, hypoglycemia unawareness, hypoglycemia unresponsiveness; glaucoma, neovascular glaucoma, cataract, retinopathy, diabetic retinopathy, diabetic maculopathy, occlusion of retinal artery, obstruction of central artery of retina, occlusion of retinal vein, macular edema, aged macular degeneration, aged disciform macular degeneration, cystoid macular edema, palpebral edema, retinal edema, chorioretinopathy, neovascular maculopathy, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, damage of skin, Skin ulcer including foot ulcer, diabetic ulcer, burn ulcer, lower leg ulcer, postoperative ulcer, traumatic ulcer, ulcer after herpes zoster, radiation ulcer, drug induced ulcer, frostbite (cold injury), chilblain, gangrene and sudden gangrene, angina pectoris, variant anguitis, coronary arteriosclero is (chronic ischemic heart disease, asymptomatic ischemic heart disease, arteriosclerotic cardiovascular disease), myocardial infarction, heart failure, congestive heart failure and painless ischemic heart disease, pulmonary edema, hypertension, pulmonary hypertension; portal hypertension; diabetic nephropathy; decubitus, renal failure.

The present composition may contain a single active ingredient or a combination of two or more active ingredients. In a combination of plural active ingredients, their respective contents may be suitably increased or decreased in consideration of their therapeutic effects and safety.

The pharmaceutical composition of the present invention may further contain the other pharmacological ingredients as far as they do not contradict the purpose of the present invention.

The present invention will be described in detail with reference to the following example, which, however, is not intended to limit the scope of the present invention.

EXAMPLE 1

Test Compound A: 11-deoxy-13,14-dihydro-15-keto-16,16-difluoro-PGE$_1$

Test Compound B: 11-deoxy-13,14-dihydro-15-keto-16,16-difluoro-PGE$_1$ isopropyl ester Male Wistar rats (7-week-old) were used in this study. Animals were anesthetized by intraperitoneal injection of thiobutabarbital sodium (80 mg/kg). Body temperature (rectal temperature) of the animals was maintained at approximately 37° C. throughout the experiment with a heating pad. After depilating the instep of the right hind limb with a depilatory cream, the cutaneous tissue blood flow was measured continuously using a non-contact type laser Doppler flowmeter (FLO-N1, Omegawave Inc., Japan). For measurements of mean arterial blood pressure, a polyethylene catheter placed in the left femoral artery was connected to a pressure transducer (TP-400T, Nihon Koden Inc., Japan) coupled to an amplifier (AP-641G, Nihon Koden Inc., Japan). The cutaneous tissue blood flow and blood pressure were recorded and analyzed using a computer system (HEM Ver. 3.5, Notocord Systems, France). Endothelin-1 (ET-1) was infused into the femoral artery at a rate of 200 pmol/kg/min with a syringe pump via the polyethylene catheter inserted retrogradely into the caudal epigastric artery branched from the right femoral artery for 15 minutes. Infusion rate of ET-1 was decreased to 20 pmol/kg/min after the termination of 200 pmol/kg/min infusion, and the decreased amount of ET-1 infusion was kept until the end of this study. The cutaneous tissue blood flow was decreased by the infusion of ET-1 into the femoral artery. When the cutaneous tissue blood flow was reached a new steady level (25 to 50 minutes after starting ET-1 infusion), vehicle or each test compound solution was administered to the animals over 2 minutes in a volume of 1 mL/kg via the polyethylene catheter placed in the left femoral vein. The administered amount of the test compound was 100 µg/kg. The cutaneous tissue blood flow and blood pressure were measured continuously and recorded every 5 minutes for 60 minutes after the administration of vehicle or each test solution.

Figure 1B:
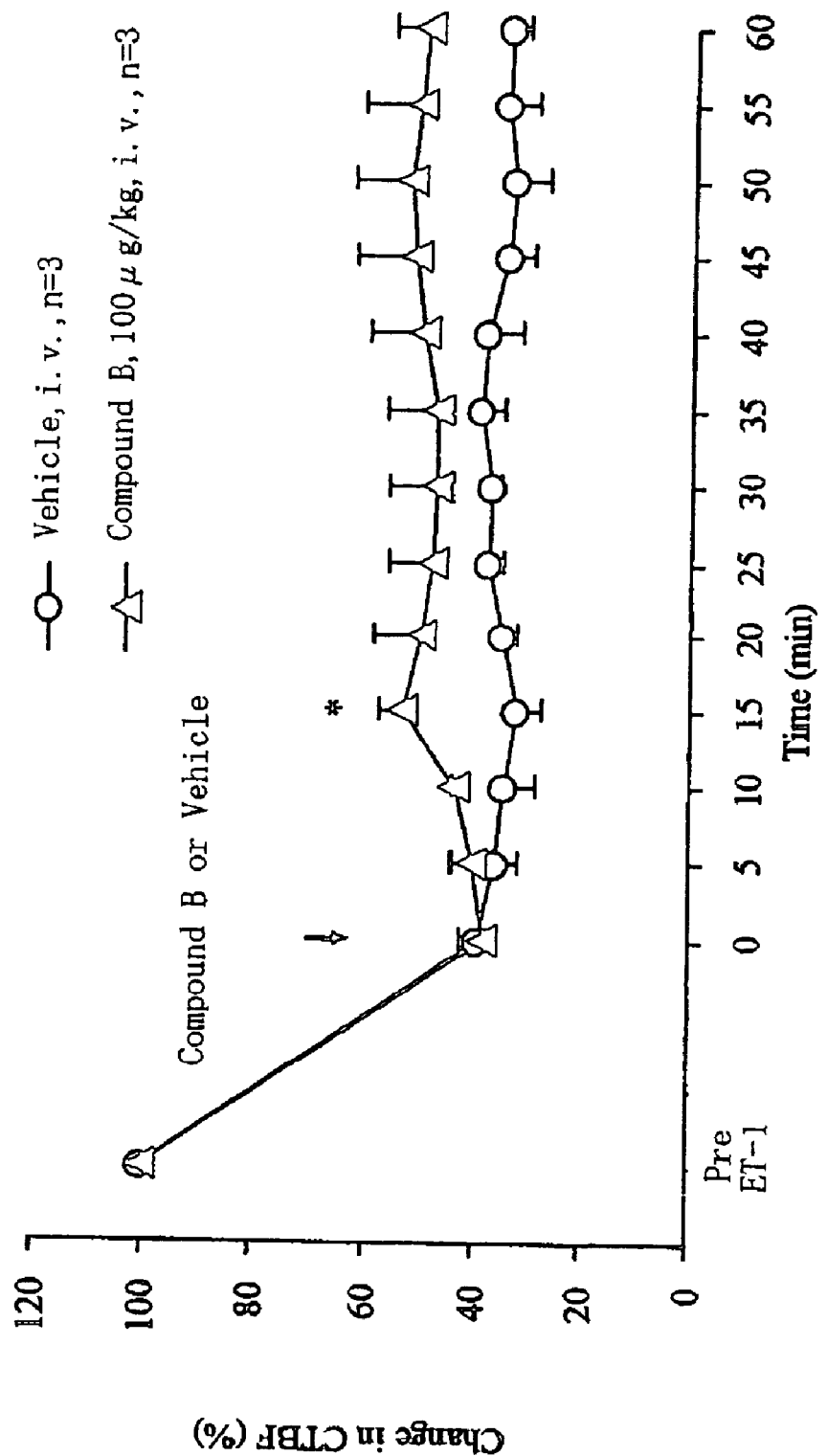
FIG. 1B is a graph showing the effect of Compound B (11-deoxy-13,14-dihydro-15-keto-16,16-difluoro-PGE$_1$ isopropyl ester) on the decreased peripheral microcirculation in rats induced by ET-1. Data are presented as mean±S.E., *p<0.05 compared with vehicle-treated control. CTBF: cutaneous tissue blood flow.

As shown in FIGS. 1A and 1B, by the femoral arterial infusion of ET-1, the cutaneous tissue blood flow was decreased to approximately 37% of the baseline value between 25 and 50 minutes after starting ET-1 infusion. There was no alteration in the cutaneous tissue blood flow by the treatment with vehicle (FIGS. 1A and 1B).

In the 100 µg/kg Compound A (11-deoxy-13,14-dihydro-15-keto-16,16-difluoro-PGE$_1$) group, the cutaneous tissue blood flow, which was decreased to approximately 35% of the baseline value by the ET-1 infusion, was significantly increased by the administration of Compound A (FIG. 1A).

In the 100 µg/kg Compound B (11-deoxy-13,14-dihydro-15-keto-16,16-difluoro-PGE$_1$ isopropyl ester) group, the cutaneous tissue blood flow, which was decreased to approximately 38% of the baseline value by the ET-1 infusion, was significantly increased by the administration of Compound B (FIG. 1B).

The blood pressure was not affected by the ET-1 infusion. Compound A and Compound B at 100 µg/kg had no significant effect on the blood pressure.

EXAMPLE 2

Test Compound A: 11-deoxy-13,14-dihydro-15-keto-16,16-difluoro-PGE$_1$

Eight male Japanese white rabbits (Std: JW/CSK) weighing approximately 2.5-3.5 kg were used in this study. The same eye of each animal was treated with the test compounds and the other eye was with the vehicle consistently throughout the study with a washout period between each treatment. Thirty microliters of each test compound solution was applied topically to one eye of each animal using a micropipette (Pipetman, Gilson, Inc., France). The contralateral control eye received an equal volume of the vehicle. The animals were dosed at approximately the same time each morning. After the animals were restrained in a holder, one drop of topical anesthetic (0.4% oxybuprocaine hydrochloride) was applied to both eyes and the IOP was measured with an applanation pneumatonometer (Model 30 Classic™, Mentor O & O, Inc., USA) before dosing, and at 1, 2, 4, 6, and 8 hours after dosing.

As shown in Table 1, Compound A significantly lowered the intraocular pressure.

TABLE 1

Intraocular Pressure (IOP) after Treatment with Test Compound

| Treatment | Concentration % | n | IOP (mmHg) Time after administration (hr) | | | | | |
| --- | --- | --- | --- | --- | --- | --- | --- | --- |
| | | | Pre | 1 | 2 | 4 | 6 | 8 |
| Vehicle | — | 8 | 16.4 ± 0.9 | 18.3 ± 1.6 | 18.9 ± 1.6 | 18.4 ± 1.3 | 19.5 ± 1.7 | 19.0 ± 1.1 |
| Compound A | 0.0016 | 8 | 17.0 ± 0.8 | 13.1 ± 0.6** | 14.5 ± 0.6* | 13.8 ± 0.8* | 15.1 ± 1.0* | 17.5 ± 1.3 |

Data are presented as mean ± SE, *p < 0.05, **p < 0.01 compared to vehicle-treated contralateral control eyes (paired Student's t-test).
Compound A: 11-deoxy-13,14-dihydro-15-keto-16, 16-difluoro-PGE$_1$

EXAMPLE 3

Diabetes was induced by single intravenous injection of 50 mg/kg streptozotocin (STZ) in 7-week-old male Crl: CD(SD) rats. Animals with plasma glucose levels 400 mg/dL or more on day 19 after the STZ treatment were used in this study. Three weeks after the STZ injection, animals were anesthetized by an intraperitoneal injection of thiobutabarbital sodium. Body temperature (rectal temperature) of the animals was maintained at approximately 37° C. throughout the experiment with a heating pad After depilating the instep of the right hind limb with a depilatory cream, the cutaneous tissue blood flow (CTBF) was measured continuously using a non-contact type laser Doppler flowmeter (FLO-N1, Omegawave Inc., Japan). The blood pressure and heart rate were simultaneously monitored. Compound A or the vehicle was intravenously administered to the animals over 10 min.

As shown in Table 2, Compound A significantly increased the cutaneous tissue blood flow as compared with the vehicle. Compound A had no effects on blood pressure (BP) and heart rate.

TABLE 2

Effect of SAG-017 on cutaneous tissue blood flow
in streptozotocin-induced diabetic rats

| Group | Dose µg/kg i.v. | n | Cutaneous Tissue Blood Flow (mL/min/100 g tissue) | | | |
|---|---|---|---|---|---|---|
| | | | Pre | Time after Initiation of Dosing (min) | | |
| | | | | 5 | 10 | 30 |
| Vehicle Control) | 0 | 5 | 3.8 ± 0.2 | 3.8 ± 0.2 | 3.7 ± 0.2 | 3.6 ± 0.2 |
| Compound A | 30 | 5 | 4.8 ± 0.5 | 6.2** ± 0.5 | 5.9** ± 0.5 | 5.2* ± 0.5 |

Data are presented as mean ± S.E., *p < 0.05, **p < 0.01 compared to vehicle control group.
Compound A: 11-deoxy-13,14-dihydro-15-keto-16,16-difluoro-$PGE_1$

EXAMPLE 4

Four months old male Kbs: J.W. rabbits were housed in aluminum cages in an animal room controlled for roomtemperature (23-24° C.), relative humidity (55-74%), ventilation rate (10-20 times/hour) and 12-hour light/dark cycle (lighting: 7:00 a.m.-7:00 p.m.). The animals were feeded with solid diet for rabbits (120 g/animal/day) and water ad libitum from automatic eatering system. The animals were subjected to at least 6 days of quarantine and acclimation. During the period, their body weight measurements and general sign observations were conducted, and the animals judged to be in good health were used in this study.

A cannula was inserted into the common carotid artery of the rabbit under inhalation anesthesia of isoflurane. Nine parts of the blood samples obtained through the cannula were mixed with 1 part of 3.8 w/v % sodium citrate. After centrifugation of the blood samples for 10 min at 1,000 rpm, platelet-rich plasma (PRP) was collected from the top layer. Then the bottom layer was further centrifuged for 15 min at 3,000 rpm, and platelet-poor plasma (PPP) was collected from the top layer. The platelet counts of the PRP and PPP fractions were performed using an ADVIA120 Hematology system (ADVIA120, Bayer Medical Ltd.). The PRP fraction was diluted with the PPP fraction so that the platelet counts was adjusted to approximately $30 \times 10^4$ cells/µL. Thus obtained PRP (0.178 mL) was put into a cuvet, and pre-incubated on a warm bath at 37° C. for about 5 minutes. Test solution (0.022 mL) containing prostaglandin E1 or Compound A was added to the PRP. One minute later, 25 µM ADP solution (0.022 mL) was added and the degree of platelet aggregation was measured using a platelet aggregation measuring device (NBS hematolaser, Nikko Bioscience Inc.). For each test solution, a duplicate test was performed on the blood samples from 3 animals. Inhibition rate (%) was evaluated by comparing the aggregation in the test substance group with that in the vehicle control group (100%).

As shown in Table 3, prostaglandin $E_1$ ($PGE_1$) inhibited platelet aggregation by 20.9%, 91.2% and 89.0% at concentrations of $1 \times 10^{-8}$, $1 \times 10^{-7}$ and $1 \times 10^{-6}$ g/mL, respectively. On the other hand, Compound A showed no effect on platelet aggregation up to the highest concentration ($1 \times 10^{-5}$ g/mL) tested. The results indicate that Compound A has no effect on platelet aggregation.

TABLE 3

| Group | Concentration (g/mL) | n | Maximum aggregation (%) | Inhibition (%) |
|---|---|---|---|---|
| Control (physiologic saline) | — | 3 | 37.5 ± 3.1 | — |
| Vehicle control | — | 3 | 36.3 ± 2.8 | — |
| Compound A | $1 \times 10^{-7}$ | 3 | 35.2 ± 3.9 | 3.0 |
| | $1 \times 10^{-6}$ | 3 | 36.2 ± 4.0 | 0.3 |
| | $1 \times 10^{-5}$ | 3 | 36.8 ± 3.1 | −1.4 |
| $PGE_1$ | $1 \times 10^{-8}$ | 3 | 28.7 ± 3.6 | 20.9 |
| | $1 \times 10^{-7}$ | 3 | 3.2 ± 0.6** | 91.2 |
| | $1 \times 10^{-6}$ | 3 | 4.0 ± 0.7** | 89.0 |

Maximum aggregation (%) represenrts the mean ± S.E of 3 rabbits.
**P < 0.01; Significant difference from vehicle control (Dunnett's multiple comparison test)

EXAMPLE 5

Male Crl: CD(SD) rats were anesthetized by an intraperitoneal injection of thiobutabarbital sodium. Body temperature (rectal temperature) of the animals was maintained at approximately 37° C. throughout the experiment with a heating pad. After depilating the instep of the right hind limb with a depilatory cream, the cutaneous tissue blood flow CTBF) was measured before and 30 minutes after intravenous administration of Compound C (11-deoxy-13,14-dihyrdo-16,16-difluoro-$PGE_1$) or the vehicle using a non-contact type laser Doppler flowmeter (FLO-N1, Omegawave Inc., Japan). The blood pressure and heart rate were also monitored.

As shown in Table 4, Compound C significantly increased the cutaneous tissue blood flow as compared with the vehicle treatment. Compound C had no effects on blood pressure and heart rate.

TABLE 4

Effect of Compound C on cutaneous tissue blood flow in rats

| Group | Dose µg/kg, i.v. | n | Cutaneous Tissue Blood Flow (mL/min/100 g tissue) | |
|---|---|---|---|---|
| | | | Before administration | After administration |
| Vehicle (Control) | 0 | 5 | 11.4 ± 1.1 | 10.4 ± 0.8 |
| Compound C | 10 | 5 | 11.6 ± 0.3 | 13.0 ± 0.2* |

Data are presented as mean ± S.E.,
*p < 0.05 compared to vehicle control group.

EXAMPLE 6

Human vascular endothelial cell culture was brought to confluence, as measured by transendothelial electrical resistance (TEER). The cell culture was then deprived of oxygen for 30 minutes by incubation in a nitrogen atmosphere. The cells were then either treated with 0.1% DMSO or with the combination of 5 nM Compound A and 0.1% DMSO (final concentrations). The cell density was determined by TEER at the indicated time points.

Figure 2A:
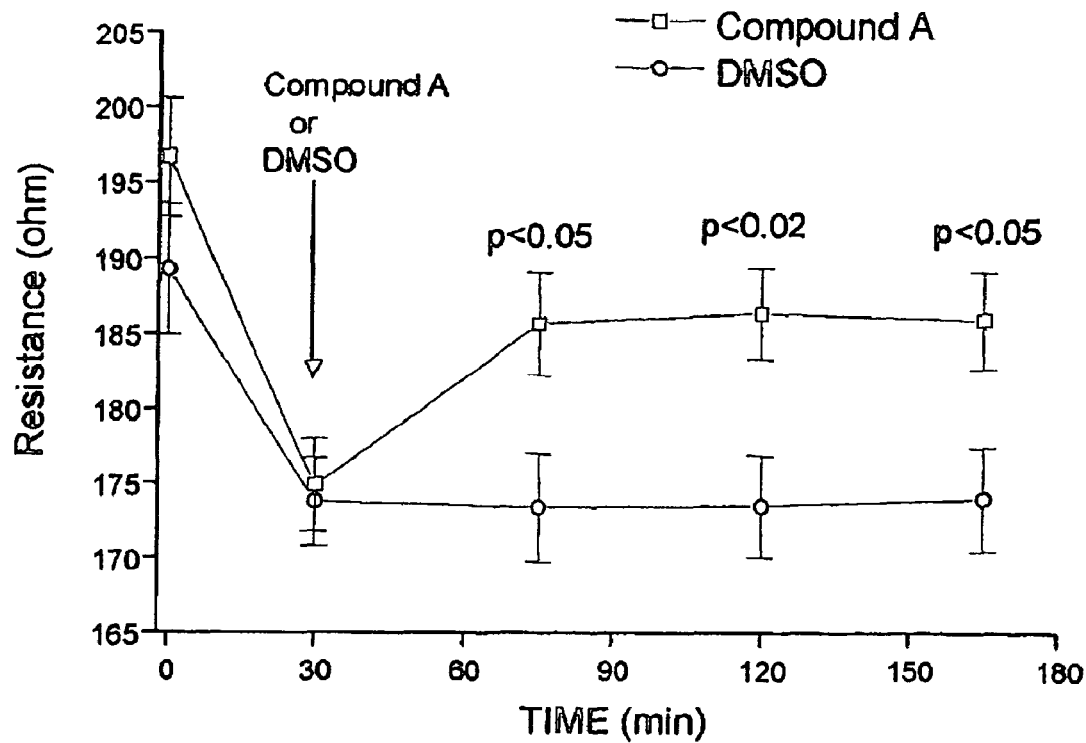
FIG. 2A is a graph showing the effect of Compound A on Recovery of Transendothelial Electrical Resistance (TEER). Human vascular endothelial cell cultures were brought to confluence, as measured by transendothelial electrical resistance (TEER). The cell cultures were then deprived of oxygen for 30 minutes by incubation in a nitrogen atmosphere. The cells were then either treated with 0.1% DMSO or with 5 nM Compound A in 0.1% DMSO. Statistical significance is indicated at all data points after drug treatment. N=10 cells.

As shown in FIG. 2A, the DMSO-treated cells showed very little recovery of TEER. The Compound A-treated cells showed immediate recovery of TEER.

The results demonstrate that the damaged TEER, a measured barrier function of endothelial cells, recovers rapidly after Compound A-treatment.

EXAMPLE 7

Human microvascular endothelial cells (adult) (HMVEC-AD) were grown to confluence. The cells were then exposed to a nitrogen atmosphere for 30 minutes and returned to the normal air atmosphere. ATP levels were monitored at the indicated time points using a luciferin-luciferase assay system (ATPlite, Perkin Elmer).

Figure 2B:
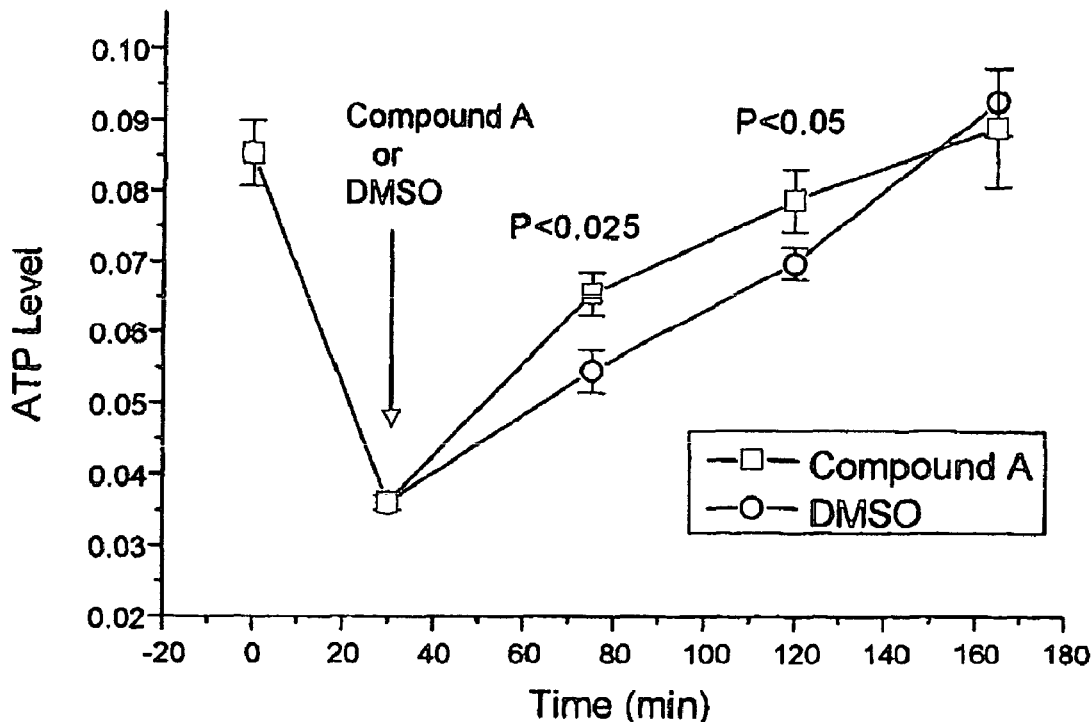
FIG. 2B is a graph showing the effect of Compound A on Recovery of the ATP Level. Human microvascular endothelial cells (adult) (HMVEC-AD) were grown to confluence. The cells were then exposed for 30 minutes to a nitrogen atmosphere and returned to the normal air atmosphere. ATP levels were monitored at the indicated time points using a luciferin-luciferase assay system (ATPlite, Perkin Elmer). ATP levels are given as relative luminescence. N=6 cells at each time point.

As shown in FIG. 2B, ATP levels decreased when the cells were exposed to the nitrogen atmosphere. ATP levels returned more quickly in the cells treated with 5 nM Compound A compared to the cells treated with 0.01% DMSO alone.

EXAMPLE 8

Male GK/Jcl rats, a spontaneous model of non-insulin-dependent diabetes, were anesthetized by an intraperitoneal injection of thiobutabarbital sodium. Body temperature (rectal temperature) of the animals was maintained at approximately 37° C. throughout the experiment with a heating pad. After depilating the instep of the right hind limb with a depilatory cream, the cutaneous tissue blood flow (CTBF) was measured before (base line) and 20 minutes after intravenous administration of Compound A or the vehicle using a non-contact type laser Doppler flowmeter (FLO-N1, Omegawave Inc., Japan). Data was expressed as % compared with the base line cutaneous tissue blood flow.

As shown in Table 5, Compound A significantly increased the cutaneous tissue blood flow in the spontaneous diabetes rats as compared with the vehicle.

TABLE 5

Effect of Compound A on cutaneous tissue blood flow in spontaneous diabetes rats

| Group | Dose µg/kg i.v. | n | Cutaneous Tissue Blood Flow compared with the base line (%) |
|---|---|---|---|
| Vehicle (Control) | 0 | 5 | 103 ± 2 |
| Compound A | 20 | 5 | 122 ± 1* |

Data are presented as mean ± S.E.,
*p < 0.05 compared to vehicle control group.

SYNTHESIS EXAMPLE 1

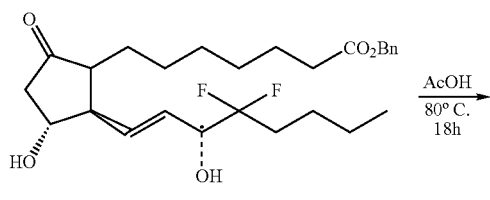

Compound (1)
100.6 mg
457.6 mg

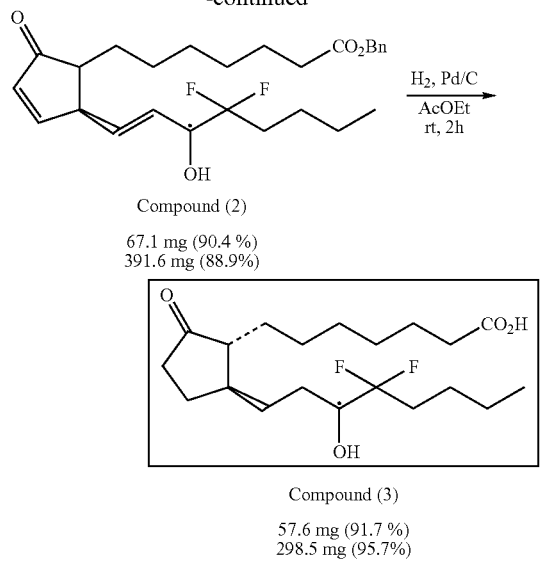

Compound (2)
67.1 mg (90.4 %)
391.6 mg (88.9%)

Compound (3)
57.6 mg (91.7 %)
298.5 mg (95.7%)

Synthesis of 16,16-difluoro-PGA$_1$ benzyl ester (2)

16,16-Difluoro-PGE$_1$ benzyl ester (1) (457.8 mg, 0.95 mmol) was dissolved in acetic acid (13.7 mL, 0.24 mol), and the solution was stirred at 80° C. for 18 hours. The reaction mixture was cooled to room temperature. 10 mL of toluene was added to the solution and concentrated under reduced pressure. This operation was repeated five times to removed acetic acid. The residue was purified by silica gel column chromatography (silica gel: FL60D (70 g), Fuji Silysia, hexane/ethyl acetate (2:1)) to obtain compound (2) as yellow oil. Yield: 391.6 mg (88.9%).

Synthesis of 11-deoxy-13,14-dihydro-16,16-difluoro-PGE$_1$ (3)

16,16-Difluoro-PGA$_1$ benzyl ester (compound (2)) (382.5 mg, 0.83 mmol) was hydrogenated in ethyl acetate (10 mL) under the presence of 10% palladium-carbon (57.4 mg, wet with 50% w/w of water) at room temperature, at atmospheric pressure for 2 hours. The reaction mixture was filtered through a Celite pad, the filter cake was washed with ethyl acetate, and then the filtrate was concentrated under reduced pressure. The residue was purified by silica gel column chromatography (silica gel BW-300SP (50 g, wet with 15% w/w of water), Fuji Silysia, hexane/ethyl acetate (1:1)) to obtain crude compound (3) (298.5 mg, 95.7%).

The crude compound (3) was combined with another lot of the crude compound. And then, totally about 350 mg of the crude compound was purified by preparative HPLC (YMC-Pack D-SIL-5-06 20×250 mm, hexane/2-propanol/acetic acid (250:5:1), 20 mL/min) to obtain compound (3) as colorless oil. Yield: 297.3 mg (HPLC purification recovery: 83.5%).

$^1$H-NMR (200 MHz, CDCl$_3$) δ
0.94 (3H, t, J=7.1 Hz), 1.22-2.29 (28H, m), 2.34 (2H, t, J=7.3 Hz), 3.65-3.81 (1H, m)

$^{13}$C-NMR (50 MHz, CDCl$_3$) δ
13.70, 22.40, 23.25, 24.32, 26.28, 26.63), 27.18, 27.58, 28.49, 29.09, 30.39, 31.77 (t, J=24.4 Hz), 33.67, 37.63, 41.05, 54.76, 72.73 (t, J=29.0 Hz), 124.09 (t, J=244.3 Hz), 179.07, 220.79.

SYNTHESIS EXAMPLE 2

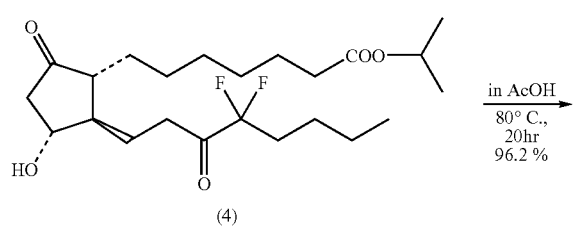

(4)

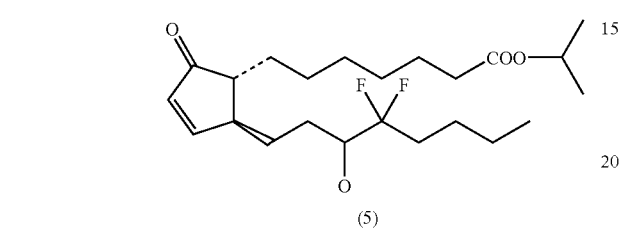

(5)

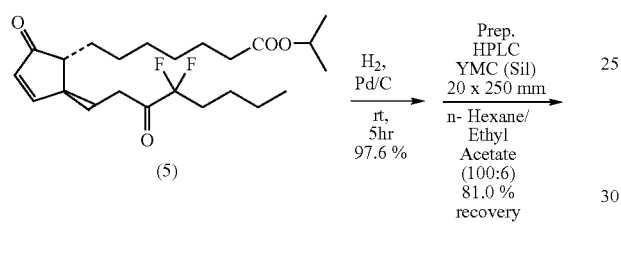

(5)

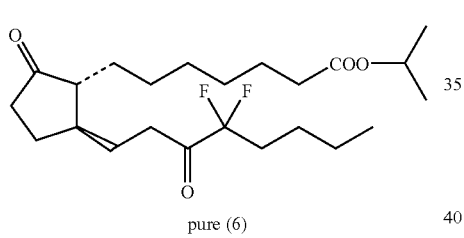

pure (6)

Figure 3:
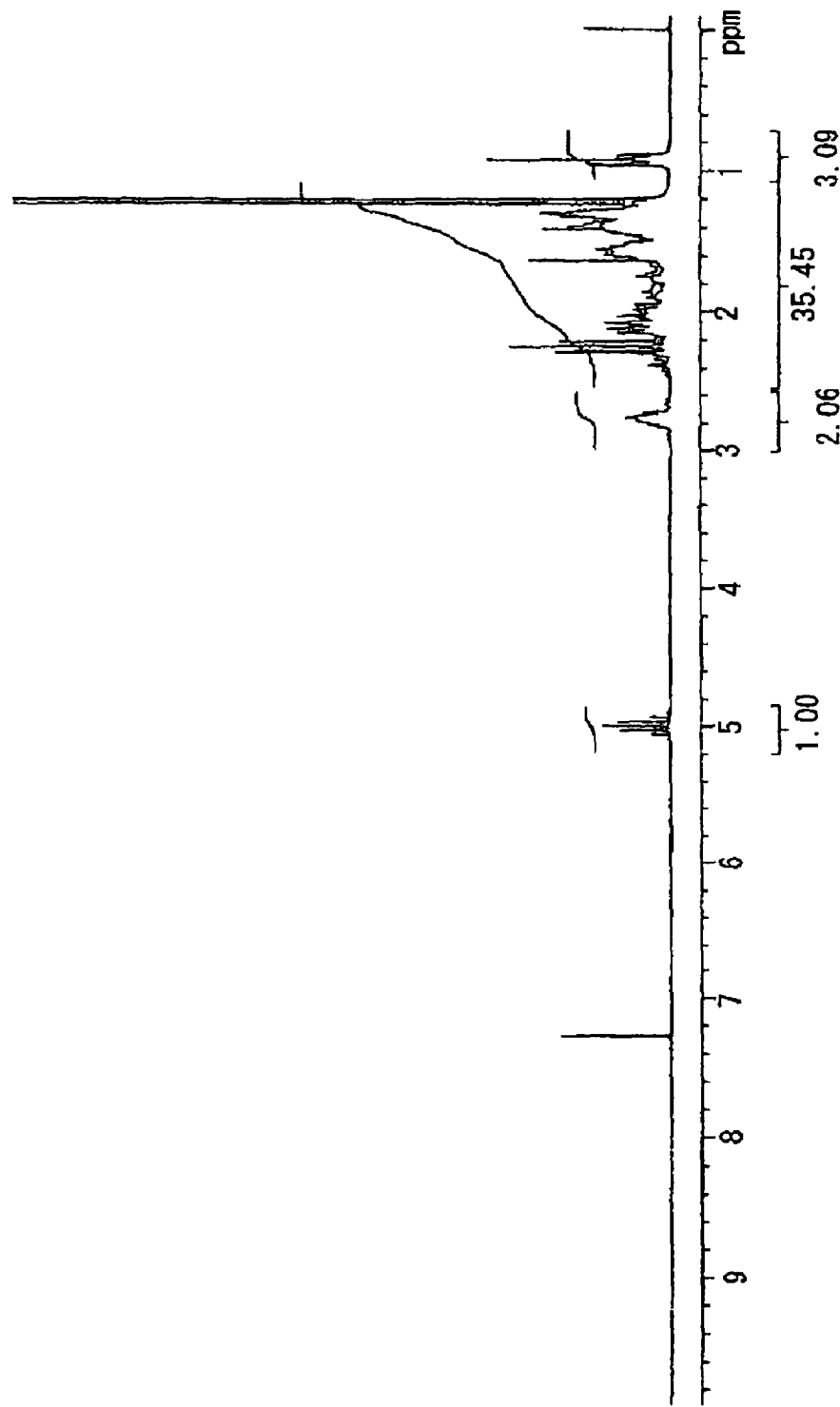
FIG. 3 is a $^1$H-NMR (200 MHz, CDCl$_3$) chart of the compound (6) obtained in Synthesis Example 2 below.
Figure 4:
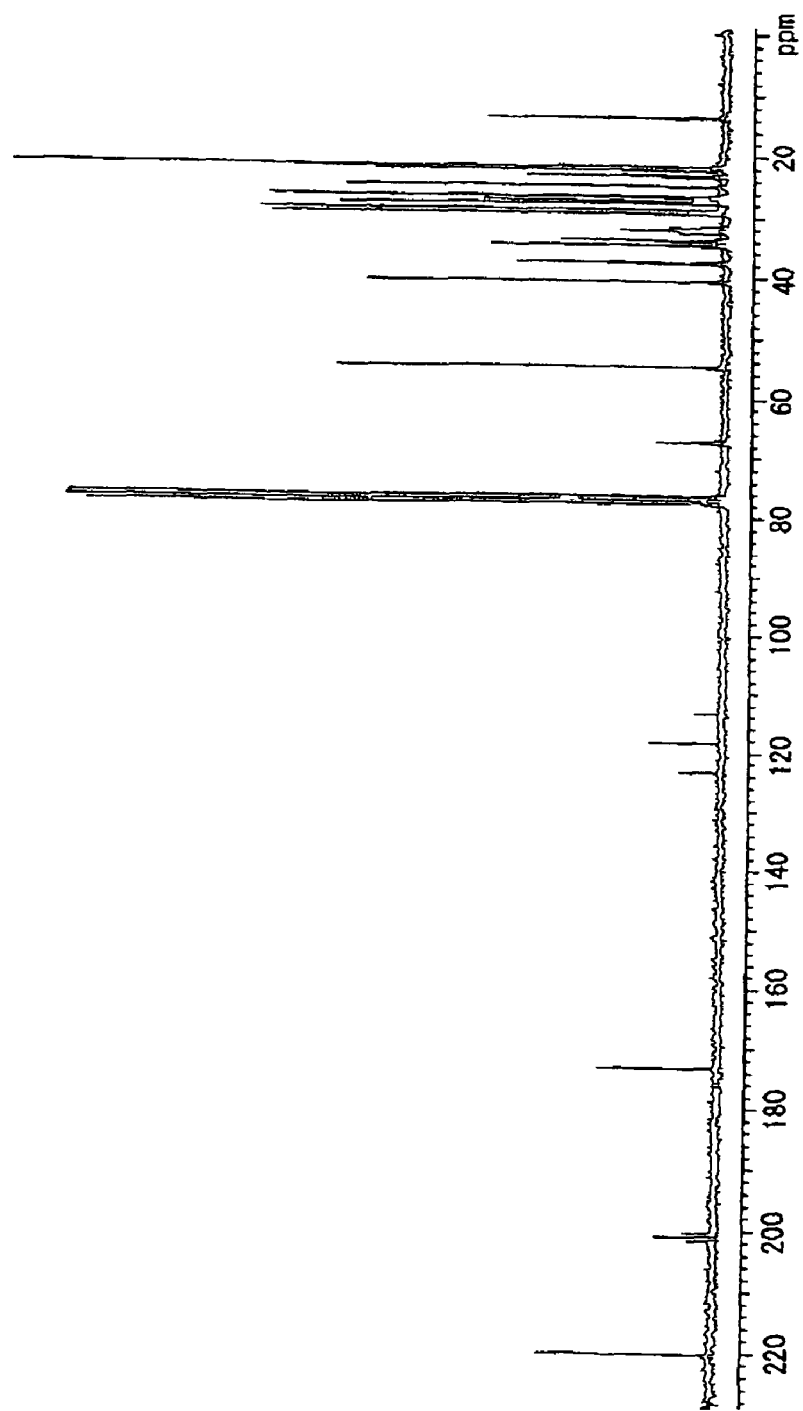
FIG. 4 is a $^{13}$C-NMR (50 MHz, CDCl$_3$) chart of the compound (6) obtained in Synthesis Example 2 below.

According to the similar manner described in Synthesis Example 1, 11-deoxy-13,14-dihydro-15-keto-16,16-difluoro-PGE$_1$ isopropyl ester (Compound (6)) was obtained as colorless oil by the above two-step reaction. Yield: 0.285 g (1$^{st}$ step: 96.2%, 2$^{nd}$ step: 97.6%, HPLC purification: recovery 81.0%). $^1$H-NMR (200 MHz, CDCl$_3$) and $^{13}$C-NMR (50 MHz, CDCl$_3$) of the Compound (6) are shown in FIGS. 3 and 4 respectively.

SYNTHESIS EXAMPLE 3

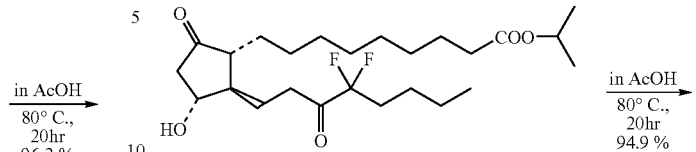

(7)

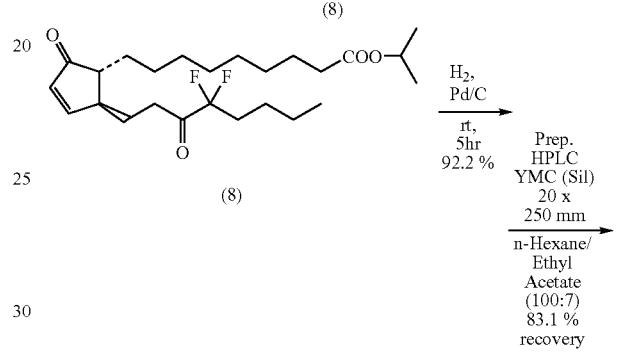

(8)

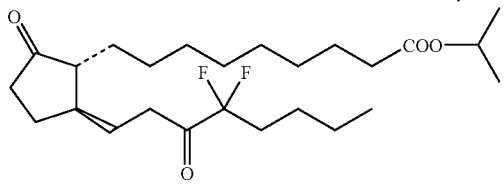

(9)

Figure 5:
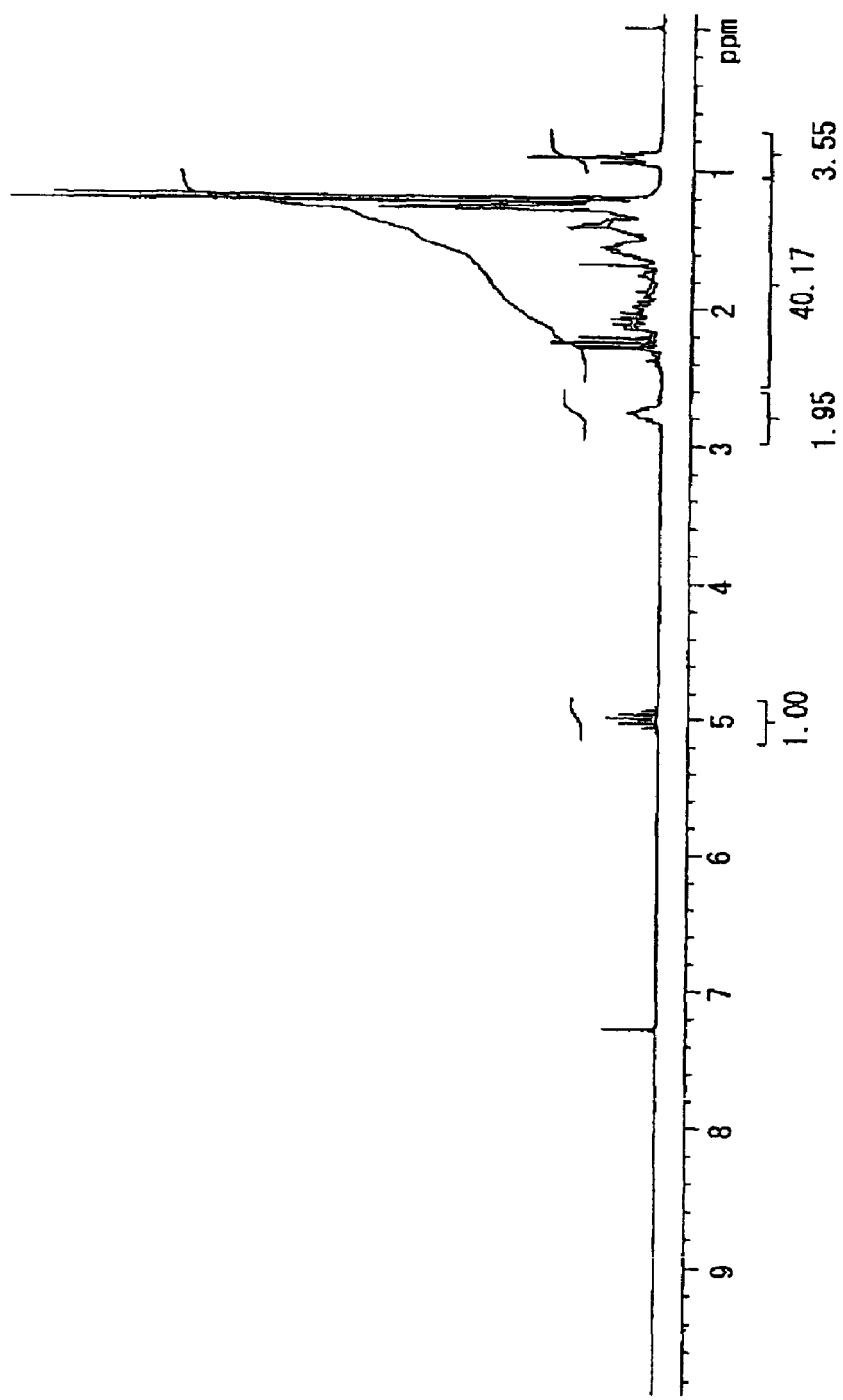
FIG. 5 is a $^1$H-NMR (200 MHz, CDCl$_3$) chart of the compound (9) obtained in Synthesis Example 3 below.
Figure 6:
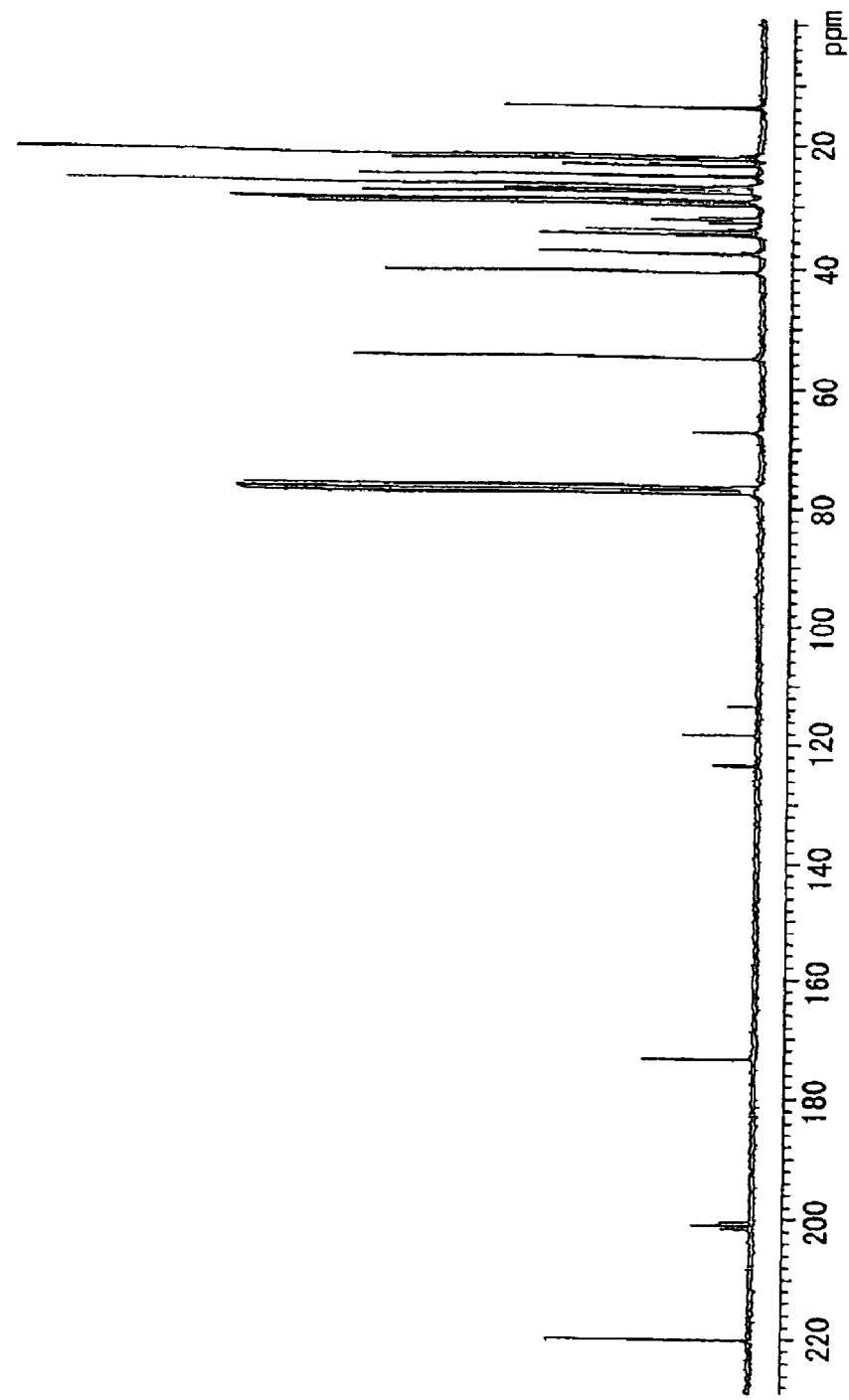
FIG. 6 is a $^{13}$C-NMR (50 MHz, CDCl$_3$) chart of the compound (9) obtained in Synthesis Example 3 below.

According to the similar manner described in Synthesis Example 1, 2-decarboxy-2-(2-carboxyethyl)-11-deoxy-13,14-dihydro-15-keto-16,16-difluoro-PGE$_1$ isopropyl ester (Compound (9)) was obtained as colorless oil. Yield: 0.402 g (1$^{st}$ step: 94.9%, 2$^{nd}$ step: 92.2%, HPLC purification: recovery 83.1%). $^1$H-NMR (200 MHz, CDCl$_3$) and $^{13}$C-NMR (50 MHz, CDCl$_3$) of the Compound (9) are shown in FIGS. 5 and 6 respectively.

SYNTHESIS EXAMPLE 4

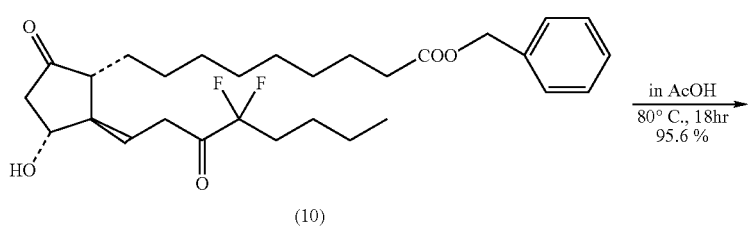

(10)

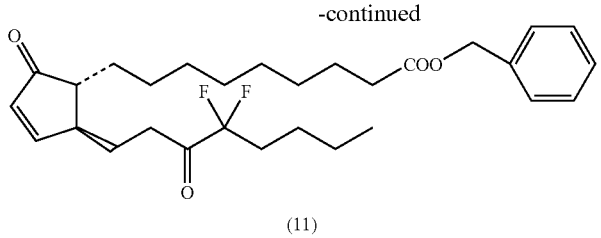

(11)

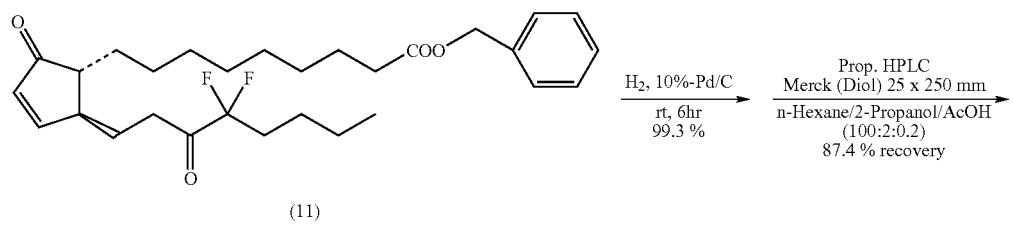

(11)

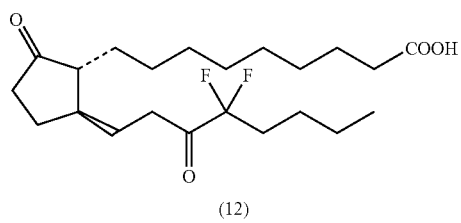

(12)

Figure 7:
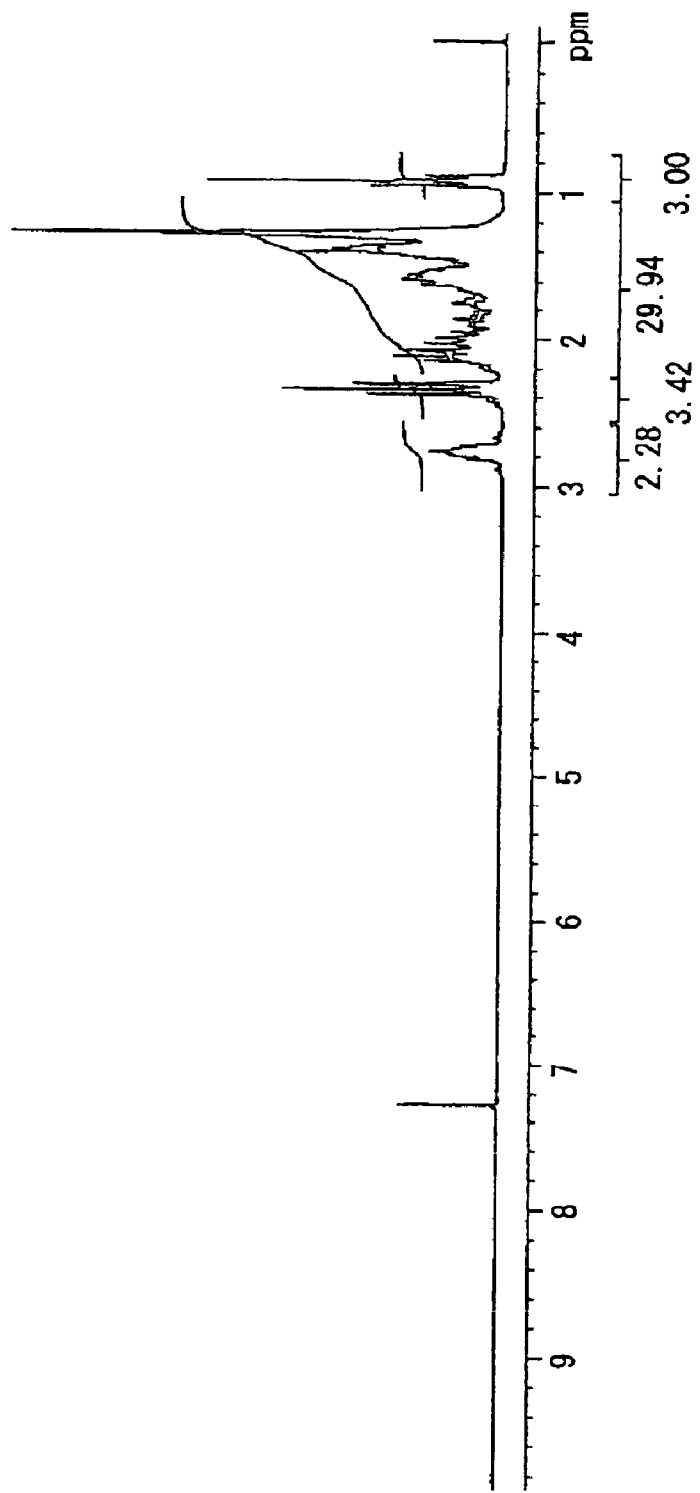
FIG. 7 is a $^1$H-NMR (200 MHz, CDCl$_3$) chart of the compound (12) obtained in Synthesis Example 4 below.
Figure 8:
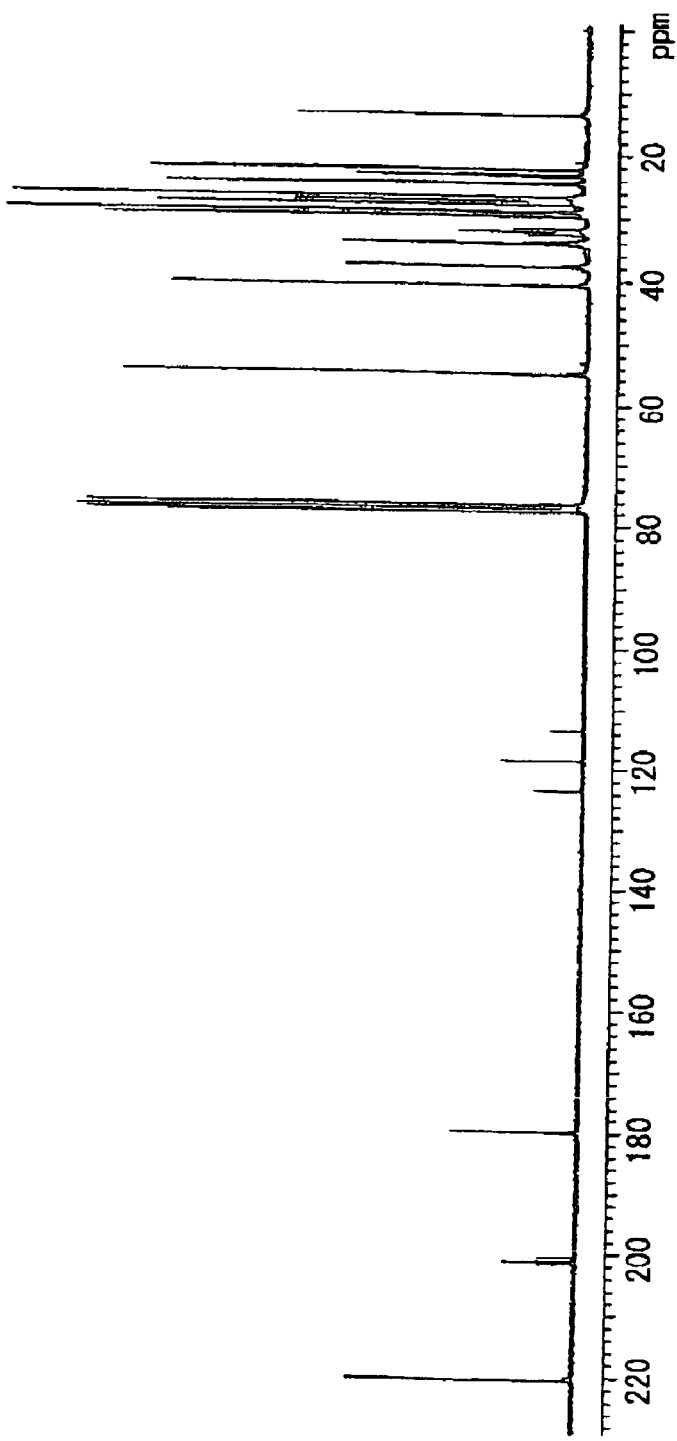
FIG. 8 is a $^{13}$C-NMR (50 MHz, CDCl$_3$) chart of the compound (12) obtained in Synthesis is Example 4 below.

According to the similar manner described in Synthesis Example 1, 2-decarboxy-2-(2-carboxyethyl)-11-deoxy-13,14-dihydro-15-keto-16,16-difluoro-PGE$_1$ (Compound (12)) was obtained as colorless oil. Yield: 0.696 g (1$^{st}$ step: 95.6%, 2$^{nd}$ step: 99.3%, HPLC purification: recovery: 87.4%). $^1$H-NMR (200 MHz, CDCl$_3$) and $^{13}$C-NMR (50 MHz, CDCl$_3$) of the Compound (12) are shown in FIGS. 7 and 8 respectively.

SYNTHESIS EXAMPLE 5

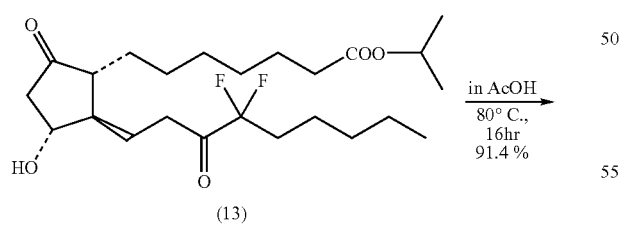

(13)

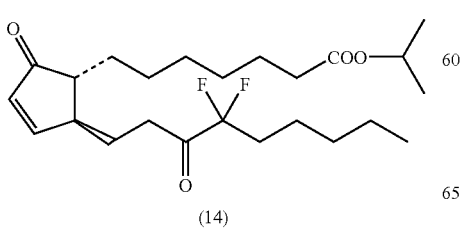

(14)

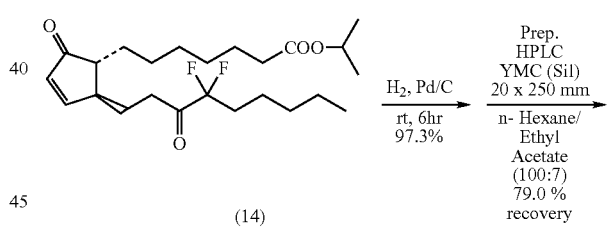

(14) → (15)

Figure 9:
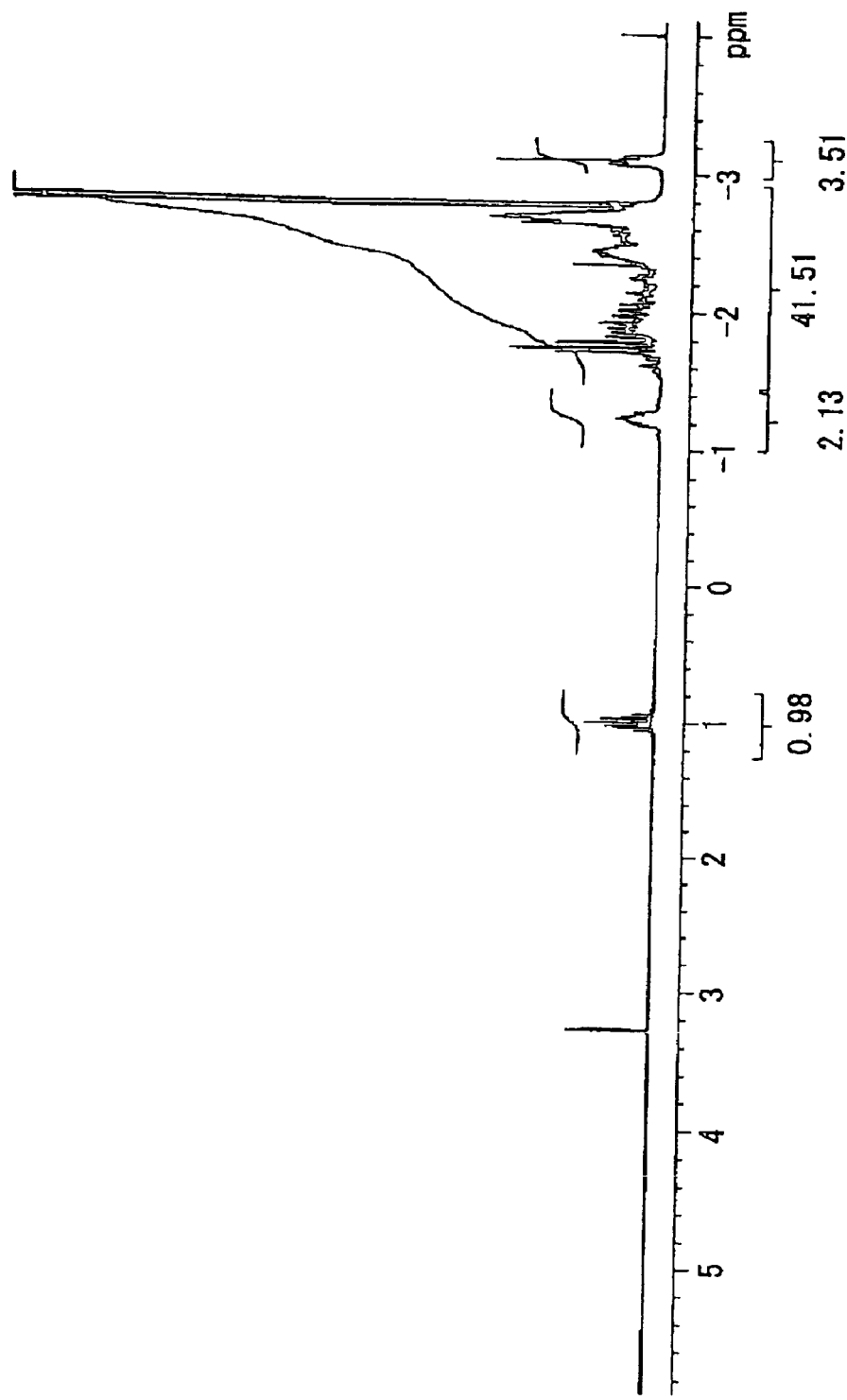
FIG. 9 is a $^1$H-NMR (200 MHz, CDCl$_3$) chart of the compound (15) obtained in Synthesis Example 5 below.
Figure 10:
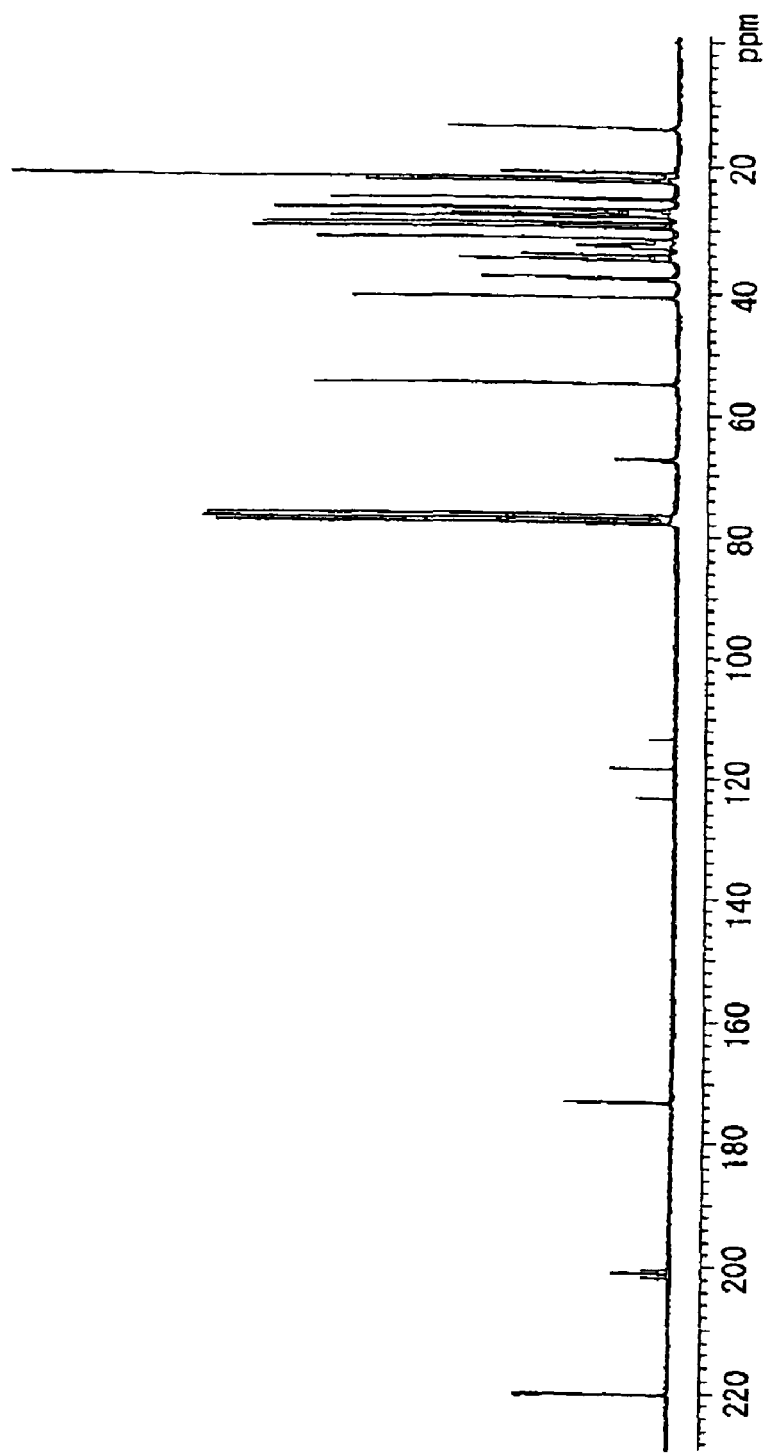
FIG. 10 is a $^{13}$C-NMR (50 MHz, CDCl$_3$) chart of the compound (15) obtained in Synthesis Example 5 below.

According to the similar manner described in Synthesis Example 1, 11-deoxy-13,14-dihydro-15-keto-16,16-difluoro-20-methyl-PGE$_1$ isopropyl ester (Compound (15)) was obtained as colorless oil. Yield: 0.271 g (1$^{st}$ step: 91.4%, 2$^{nd}$ step: 97.3%, HPLC purification: recovery: 79.0%). $^1$H-NMR (200 MHz, CDCl$_3$) and $^{13}$C-NMR (50 MHz, CDCl$_3$) of the Compound (15) are shown in FIGS. 9 and 10 respectively.

Figure 11:
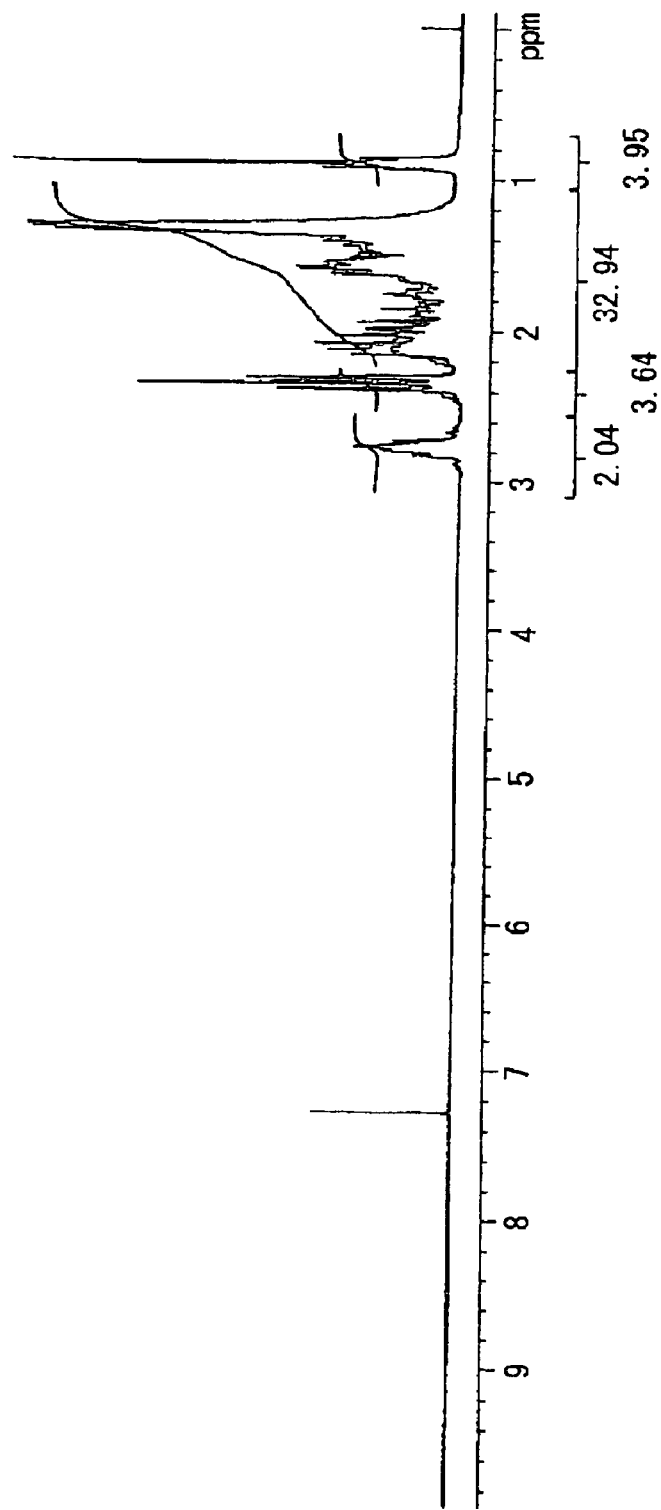
FIG. 11 is a $^1$H-NMR (200 MHz, CDCl$_3$) chart of the compound (18) obtained in Synthesis Example 6 below.
Figure 12:
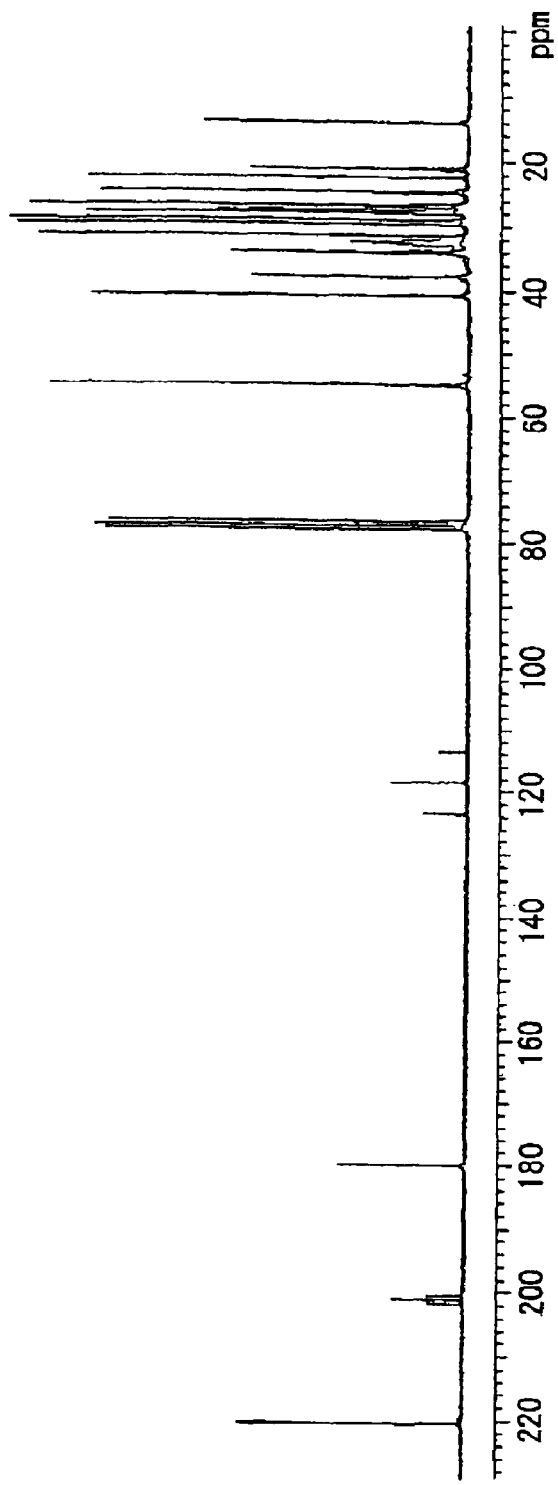
FIG. 12 is a $^{13}$C-NMR (50 MHz, CDCl$_3$) chart of the compound (18) obtained in Synthesis Example 6 below.

SYNTHESIS EXAMPLE 6
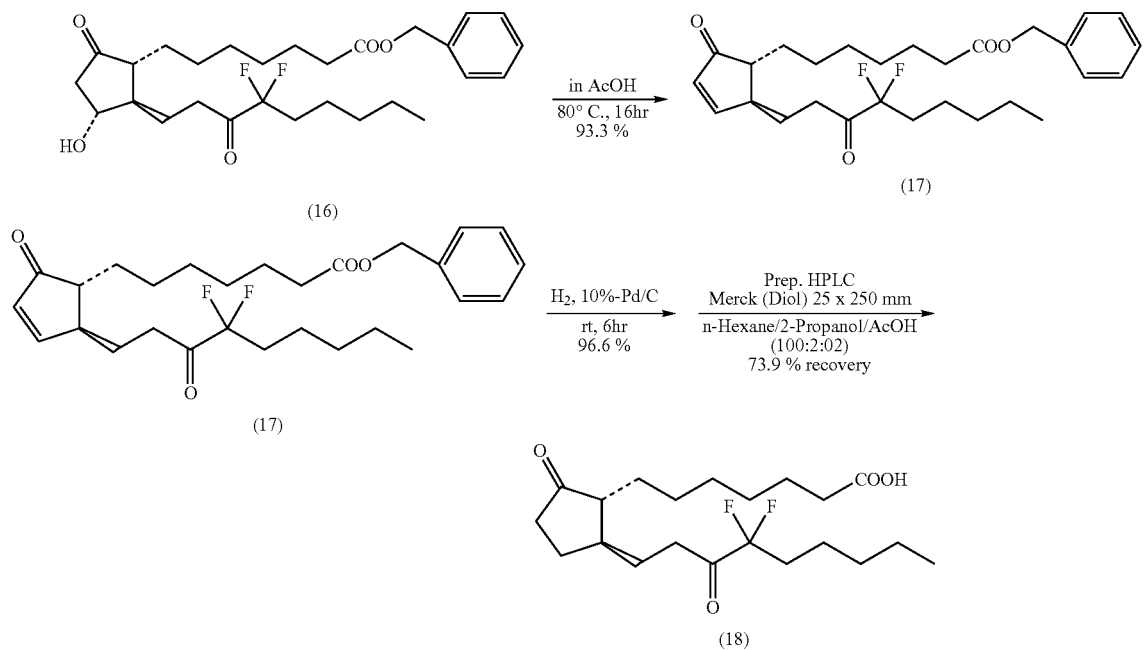
According to the similar manner described in Synthesis Example 1, 11-deoxy-13,14-dihydro-15-keto-16,16-difluoro-20-methyl-PGE$_1$ (Compound (18)) was obtained as colorless oil. Yield: 0.637 g (1$^{st}$ step: 93.3%, 2$^{nd}$ step: 96.6%, HPLC purification: recovery: 73.9%). $^1$H-NMR (200 MHz, CDCl$_3$) and $^{13}$C-NMR (50 MHz, CDCl$_3$) of the Compound (18) are shown in FIGS. 11 and 12 respectively.
SYNTHESIS EXAMPLE 7
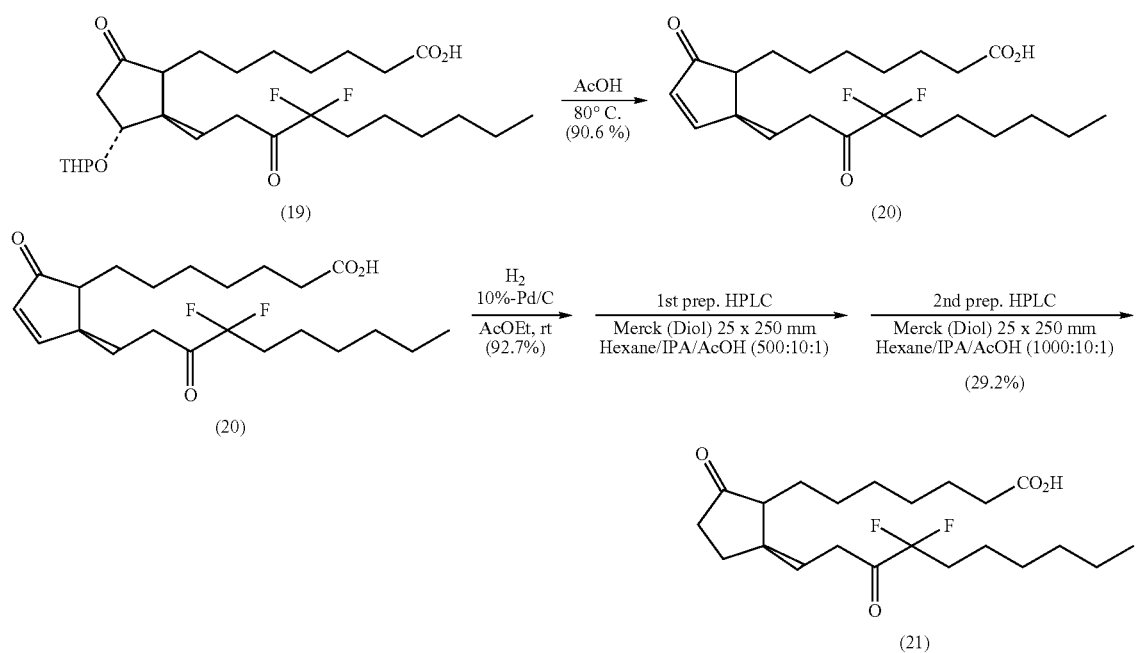

Figure 13:
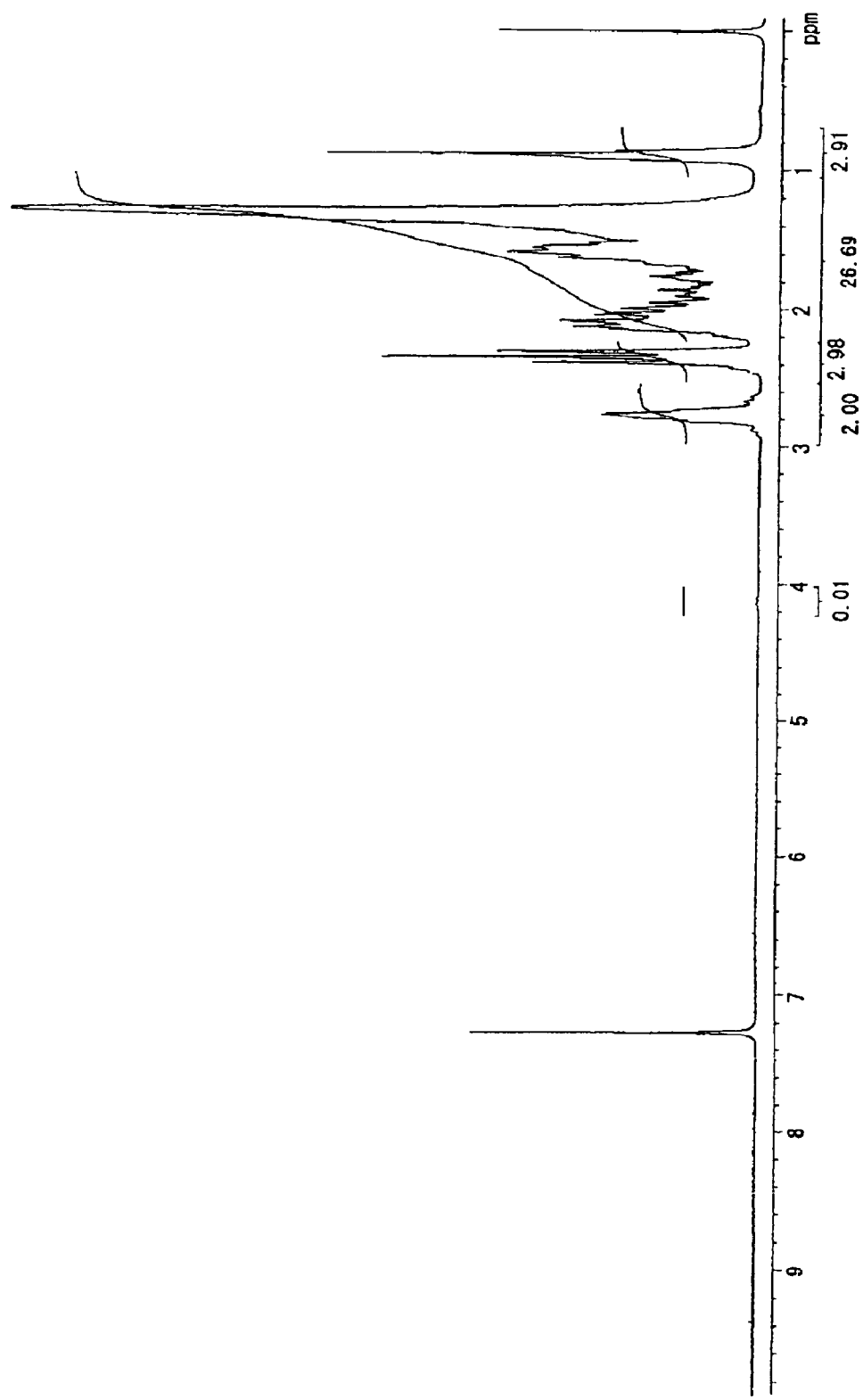
FIG. 13 is a $^1$H-NMR (200 MHz, CDCl$_3$) chart of the compound (21) obtained in Synthesis Example 7 below.
Figure 14:
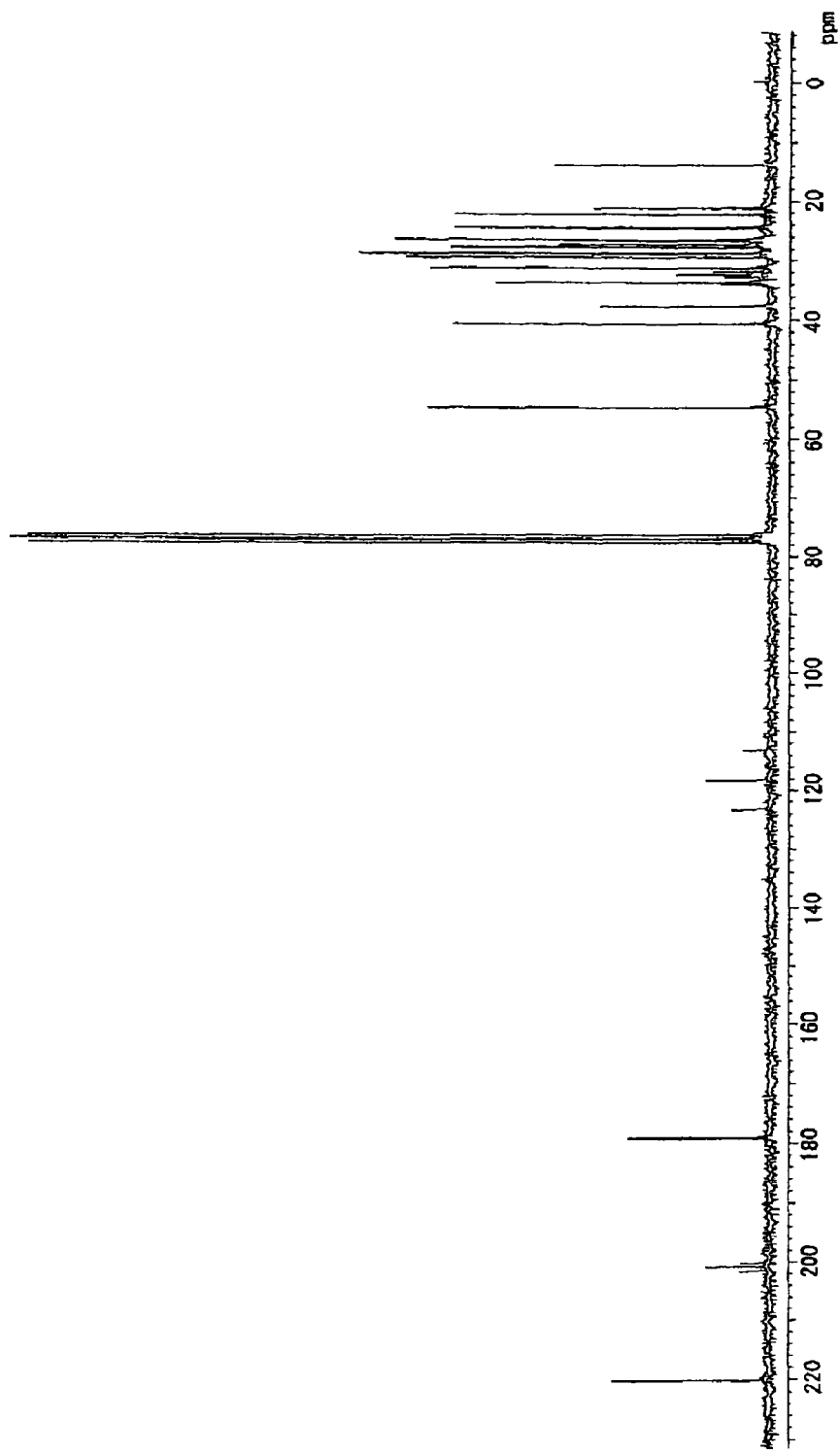
FIG. 14 is a $^{13}$C-NMR (50 MHz, CDCl$_3$) chart of the compound (21) obtained in Synthesis Example 7 below.

According to the similar manner described in Synthesis Example 1, 11-deoxy-13,14-dihydro-15-keto-16,16-difluoro-20-ethyl-PGE$_1$ (Compound (21)) was obtained as colorless oil. Yield: 0.401 g (1$^{st}$ step: 90.6%, 2$^{nd}$ step: 92.7%, HPLC purification: recovery: 29.2%). $^1$H-NMR (200 MHz, CDCl$_3$) and $^{13}$C-NMR (50 MHz, CDCl$_3$) of the Compound (21) are shown in FIGS. 13 and 14 respectively.

SYNTHESIS EXAMPLE 8

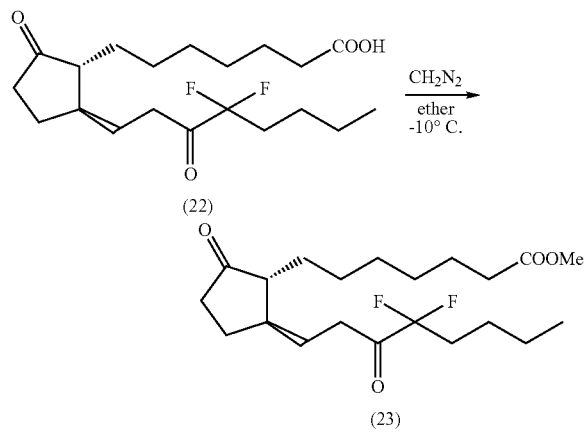

11-deoxy-13,14-dihydro-15-keto-16,16-difluoro-PGE$_1$ methyl ester (Compound (23)) was obtained as colorless oil by esterification of compound (22) with diazomethlane.

Figure 15:
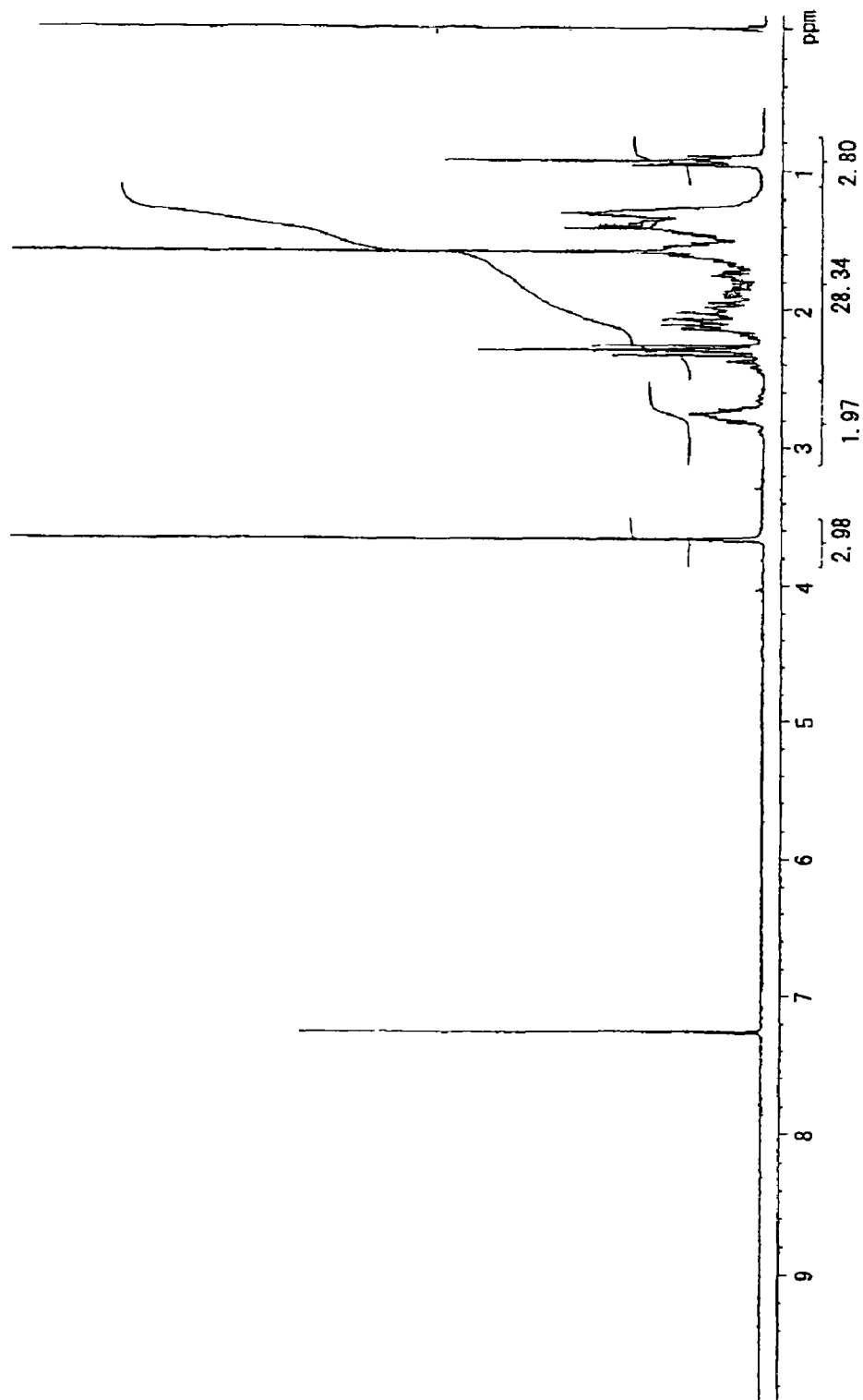
FIG. 15 is a $^1$H-NMR (200 MHz, CDCl$_3$) chart of the compound (23) obtained in Synthesis Example 8 below.
Figure 16:
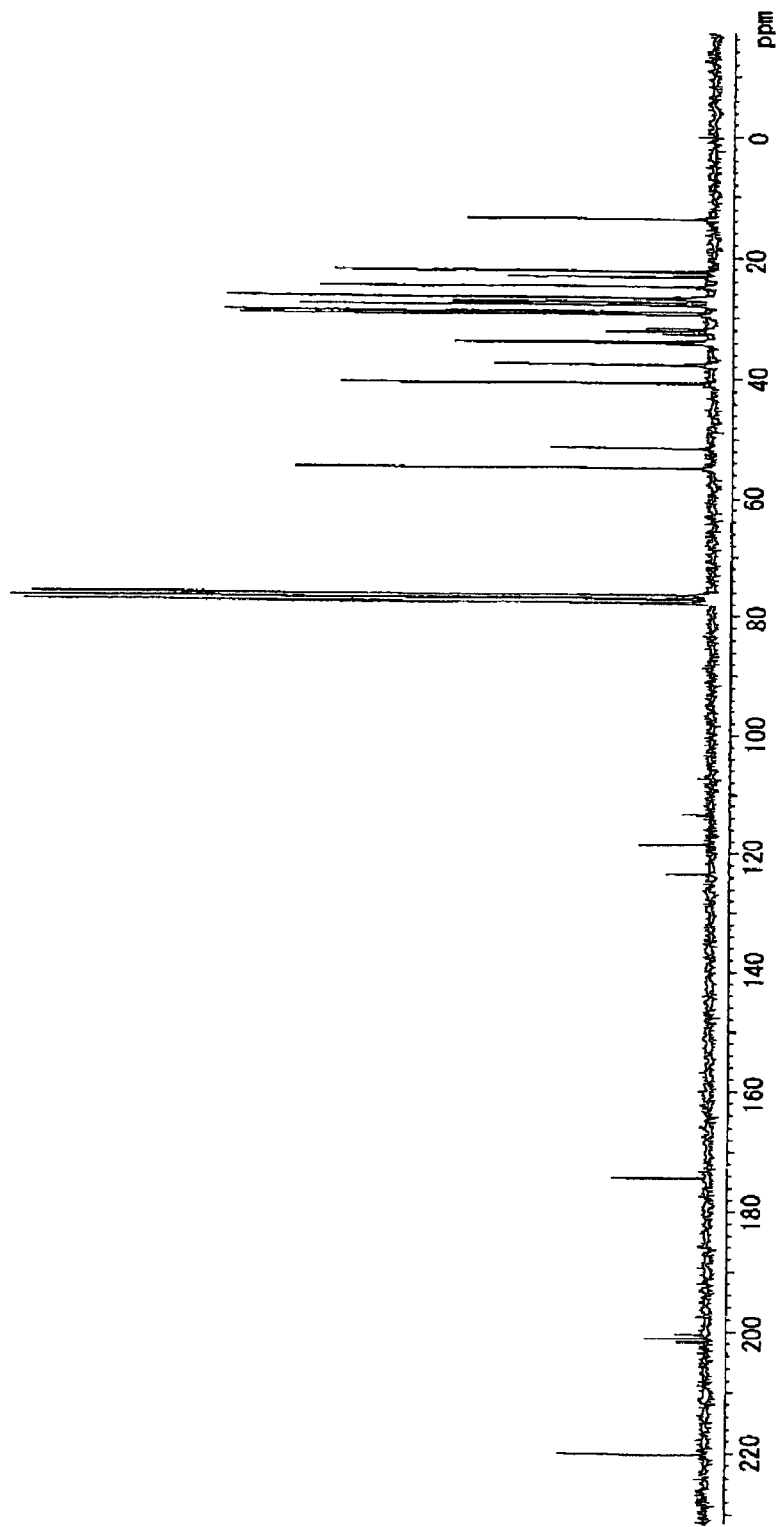
FIG. 16 is a $^{13}$C-NMR (50 MHz, CDCl$_3$) chart of the compound (23) obtained in Synthesis Example 8 below.

Yield: 0.860 g (72.9%, after purification by silica gel column chromatography). $^1$H-NMR (200 MHz, CDCl$_3$) and $^{13}$C-NMR (50 MHz, CDCl$_3$) of the Compound (23) were shown in FIGS. 15 and 16.

SYNTHESIS EXAMPLE 9

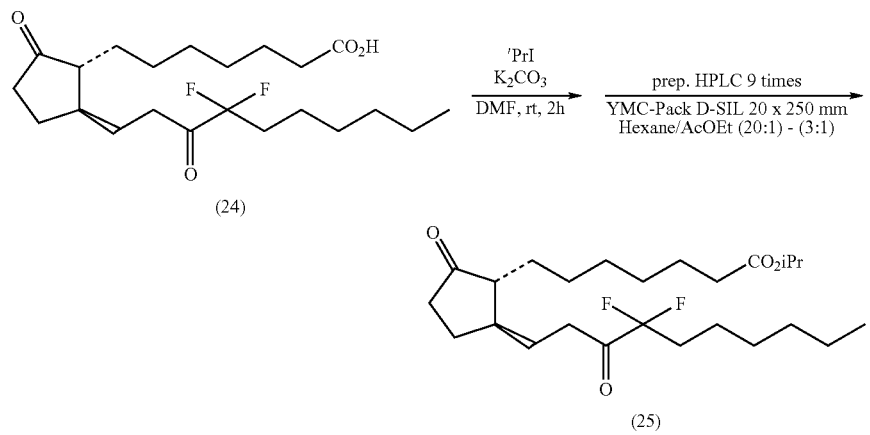

Compound (24) (0.67 g, 1.66 mmol) was dissolved in DMF (13 mL), and added K$_2$CO$_3$ (460.1 mg, 3.33 mmol) and isopropyl iodide (831 μL, 8.32 mmol). The solution was stirred at room temperature for 2 hours. The reaction mixture was cooled with ice, added water (10 mL) and brine, and extracted with ethyl acetate (30 mL) The organic layer was washed with brine (10 mL), dried with anhydrous magnesium sulfate, and then concentrated under reduced pressure. The residue was purified by silica gel column chromatography (silica gel FL60D (50 g), Fuji Silysia, hexane/ethyl acetate (5:1)) to obtain crude 11-deoxy-13,14-dihydro-15-keto-16,16-difluoro-20-ethyl-PGE$_1$ isopropyl ester (compound (25)) (0.70 g, 94.6%). The crude compound (25) was purified by preparative HPLC to obtain compound (25) as colorless oil.

Figure 17:
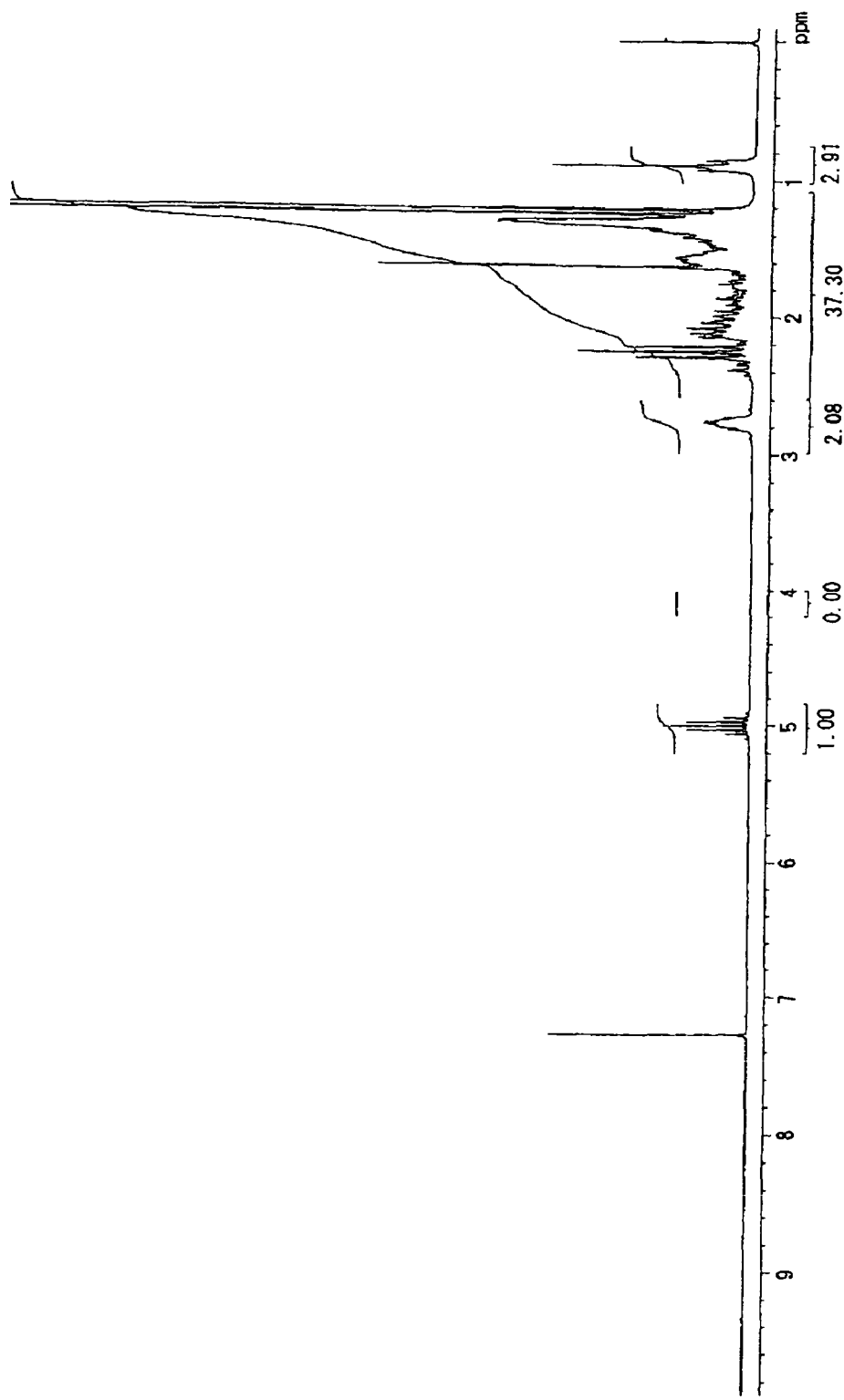
FIG. 17 is a $^1$H-NMR (200 MHz, CDCl$_3$) chart of the compound (25) obtained in Synthesis Example 9 below.
Figure 18:
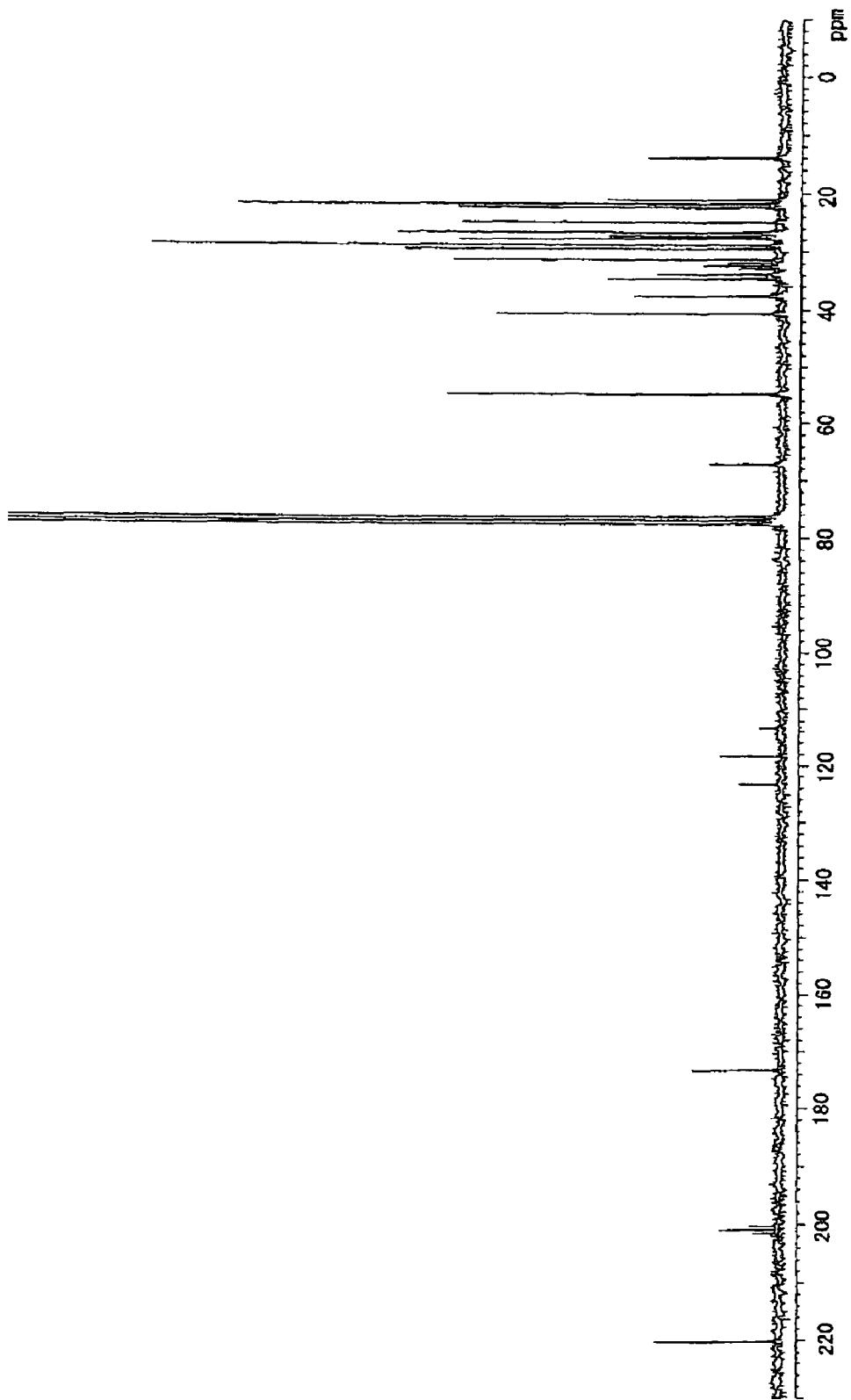
FIG. 18 is a $^{13}$C-NMR (50 MHz, CDCl$_3$) chart of the compound (25) obtained in Synthesis Example 9 below.

Yield 245.8 mg (35.1%). $^1$H-NMR (200 MHz, CDCl$_3$) and $^{13}$C-NMR (50 MHz, CDCl$_3$) for the Compound (25) are shown in FIGS. 17 and 18 respectively.

SYNTHESIS EXAMPLE 10

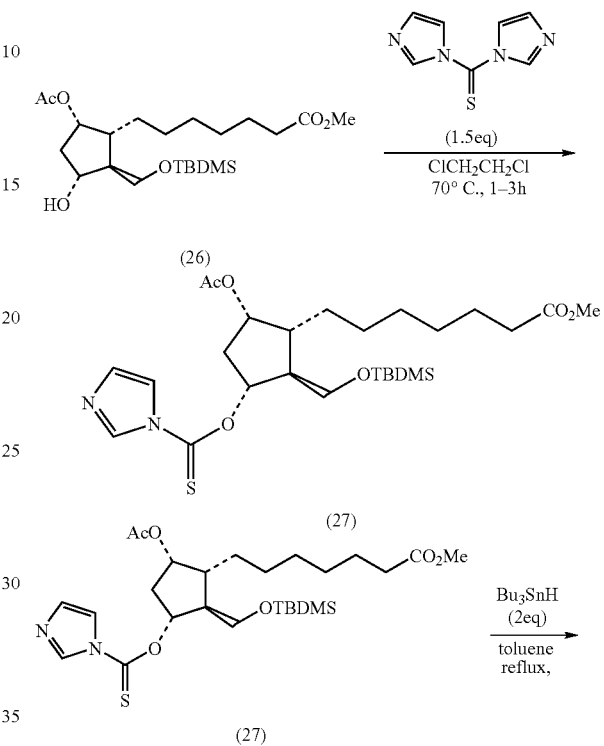

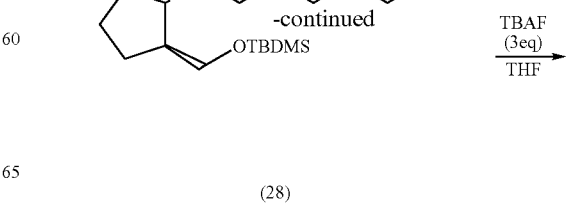

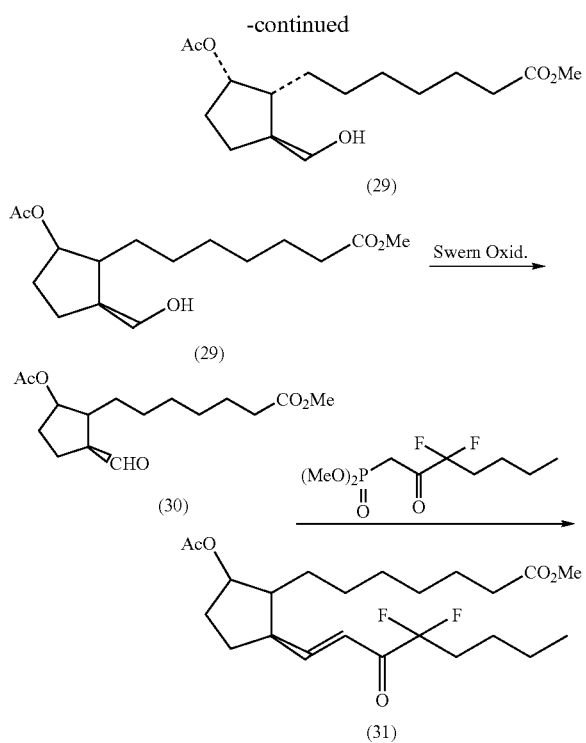

Compound (26) (8.71 g, 20.2 mmol) was dissolved in 1,2-dichloroethane (70 mL) and added 1,1'-Thiocarbonyldiimidazole (5.41 g, 30.3 mmol). The solution was stirred at 70° C. for an hour. The reaction mixture was cooled to room temperature, and then concentrated under reduced pressure. The residue Was purified by silica gel column chromatography (silica gel BW-300SP (650 g), Fuji Silysia, hexane/ethyl acetate (1:1)) to obtain compound (27) as light yellow oil (10.61 g, 97.0%).

$Bu_3SnH$ (11.21 g, 38.5 mmol) was dissolved in toluene (224 mL), and refluxed by heating. The solution of Compound (27) (10.41 g, 19.2 mmol) in toluene (208 mL) was dropped to the reaction mixture at a reflux temperature for 70 minutes. And then, the reaction mixture was cooled to room temperature, concentrated under reduced pressure to obtain crude compound (28) as light yellow oil.

The crude compound (28) (19.2 mmol) was dissolved in THF (52 mL) and TBAF solution (1.0M in THF, 38.5 mL, 38.5 mmol) was dropped for 10 minutes. After an hour, TBAF solution (1.0M in THF, 19.2 mL, 19.2 mmol) was dropped to the solution. After stirring for total 3.5 hours, the reaction mixture was concentrated under reduced pressure. The residue was purified by silica gel column chromatography (silica gel BW-300SP (1,000 g), Fuji Silysia, hexane/ethyl acetate (1:1)) to obtain compound (29) as yellow oil (4.01 g, 69.3%).

Compound (31) was obtained from compound (29) by Swern oxidation and introduction of ω-chain.

Compound (31) (807.4 mg, 1.88 mmol) was hydrogenated in ethyl acetate (8 mL) under the presence of 10% palladium-

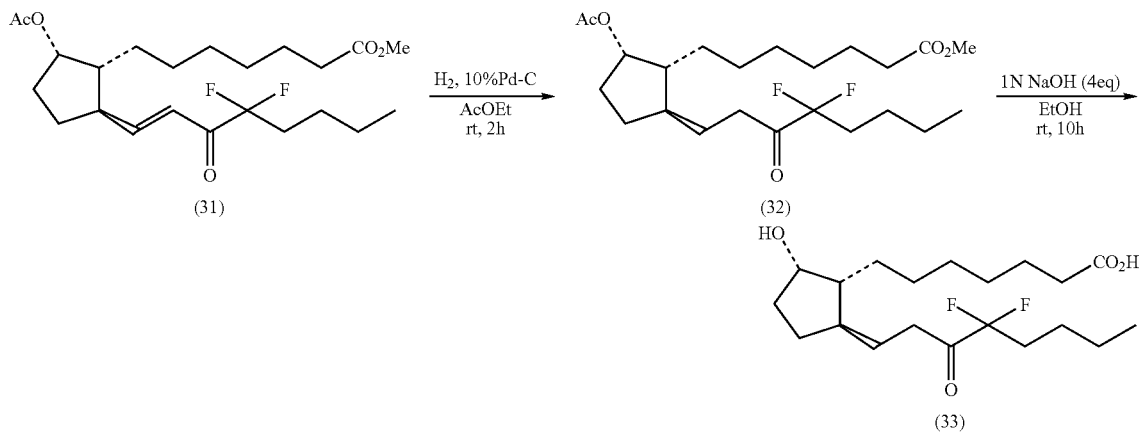

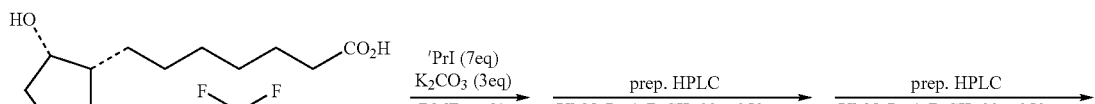

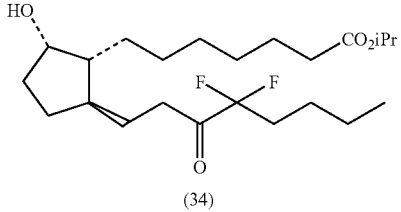

carbon at room temperature for 2 hours. The reaction mixture was filtered through a Celite pad, and the filtrate was concentrated under reduced pressure to obtain crude compound (32) as the light brown oil.

The crude compound (32) (1.88 mmol) was dissolved in EtOH (8 mL). 1N—NaOH solution (7.4 mL, 7.4 mol) was dropped to the solution at room temperature for 10 minutes. The reaction mixture was stirred at room temperature for 10 hours, and then cooled with ice. 1N—HCl (7.1 mL) was dropped to the reaction mixture to adjust pH around 3-4. Then the reaction mixture was extracted with TBME (30 mL). The organic layer was washed with water (10 mL) and brine (10 mL), dried with anhydrous magnesium sulfate, and then concentrated under reduced pressure. The residue was purified by silica gel column chromatography (silica gel 15% water including FL-60D (80 g), Fuji Silysia, hexane/ethyl acetate (2:1)) to obtain compound (33) as light yellow oil (481.4 mg, 68.8%).

Figure 19:
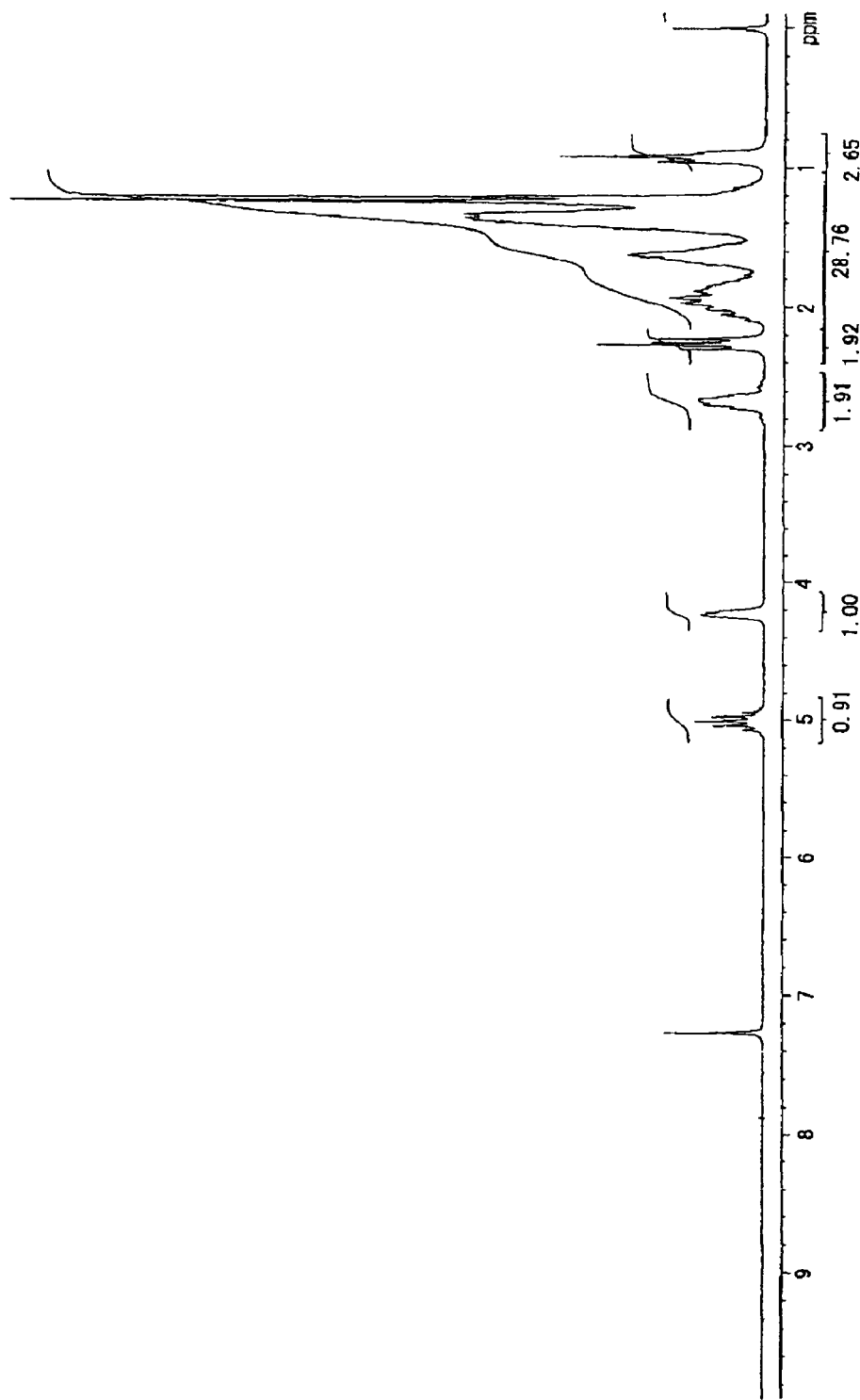
FIG. 19 is a $^1$H-NMR (200 MHz, CDCl$_3$) chart of the compound (34) obtained in Synthesis Example 10 below.
Figure 20:
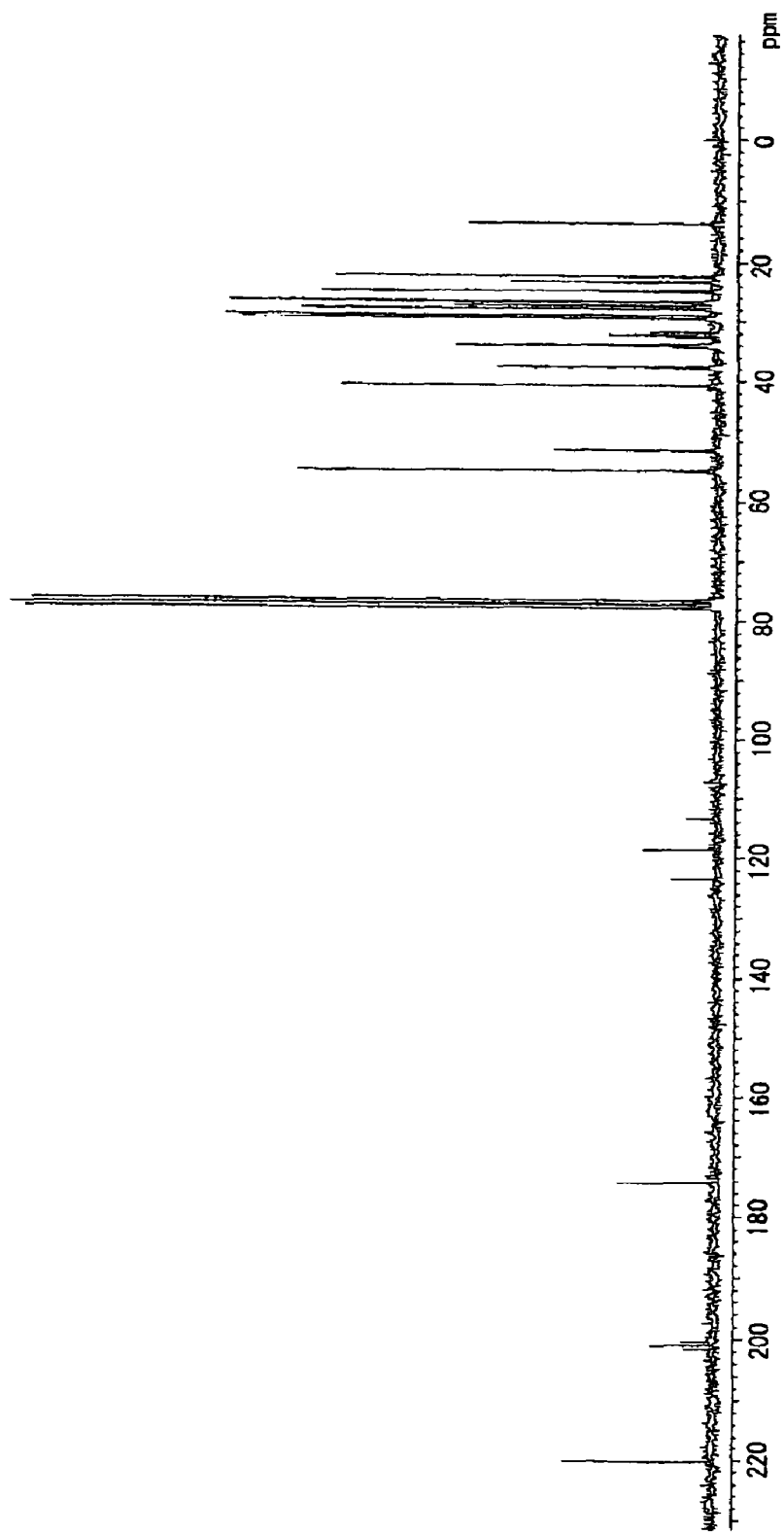
FIG. 20 is a $^{13}$C-NMR (50 MHz, CDCl$_3$) chart of the compound (34) obtained in Synthesis Example 10 below.

According to the similar manner described in Synthesis Example 9, 11-deoxy-13,14-dihydro-15-keto-16,16-difluoro-$PGF_{1\alpha}$ isopropyl ester (compound (34)) was obtained from compound (33) as colorless oil. Yield: 166.6 mg (reaction step 91.9%; HPLC purification: recovery: 55.4%). $^1$H-NMR (200 MHz, $CDCl_3$) and $^{13}$C-NMR (50 MHz, $CDCl_3$) of the Compound (34) are shown in FIGS. 19 and 20 respectively.

The invention claimed is:

1. A method for treating a peripheral vascular disease in a mammalian subject, which comprises administering an effective amount of an 11-deoxy-prostaglandin compound to the subject in need of treatment of a peripheral vascular disease,
wherein the treating comprises the care, relief, attenuation or arrest of progression of the peripheral vascular disease,
wherein said 11-deoxy-prostaglandin compound is a compound represented by the following formula (III):

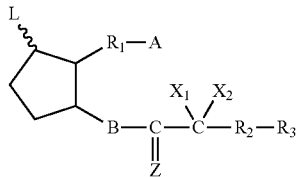

(III)

wherein L is hydrogen, hydroxy or oxo, wherein the five-membered ring may optionally have at least one double bond;
A is —$CH_3$, —$CH_2OH$, —$COCH_2OH$, —COOH or a salt, ether, ester or amide thereof;
B is —$CH_2$—$CH_2$—;
Z is

wherein $R_4$ and $R_5$ are hydrogen or hydroxy, wherein $R_4$ and $R_5$ are not hydroxy at the same time;
$X_1$ and $X_2$ are hydrogen or halogen;
$R_1$ is a saturated or unsaturated bivalent lower or medium aliphatic hydrocarbon;
$R_2$ is a single bond or lower alkylene; and
$R_3$ is lower alkyl.

2. The method as described in claim 1, wherein said 11-deoxy-prostaglandin compound is an 11-deoxy-13,14-dihydro-15-keto-prostaglandin compound.

3. The method as described in claim 1, wherein said 11-deoxy-prostaglandin compound is an 11-deoxy-13,14-dihydro-16-mono or dihalogen-prostaglandin compound.

4. The method as described in claim 1, wherein said 11-deoxy-prostaglandin compound is an 11-deoxy-13,14-dihydro-15-keto-16-mono or dihalogen-prostaglandin compound.

5. The method as described in claim 1, wherein said 11-deoxy-prostaglandin compound is an 11-deoxy-13,14-dihydro-15-keto-16-mono or difluoro-prostaglandin compound.

6. The method as described in claim 1, wherein said 11-deoxy-prostaglandin compound is an 11-deoxy-13,14-dihydro-15-keto-16-mono or dihalogen-prostaglandin E or F compound.

7. The method as described in claim 1, wherein said prostaglandin compound is an 11-deoxy-13,14-dihydro-15-keto-16-mono or difluoro-prostaglandin E or F compound.

8. The method as described in claim 1, wherein said prostaglandin compound is an 11-deoxy-13,14-dihydro-15-keto-16,16-difluoro-prostaglandin $E_1$ compound.

9. The method as described in claim 1, wherein said peripheral vascular disease is peripheral arterial disease.

10. The method as described in claim 9, wherein said peripheral arterial disease is arteriosclerosis.

11. A method for treating damaged peripheral vascular wall in a mammalian subject, which comprises administering an effective amount of an 11-deoxy-prostaglandin compound the subject in need of treatment of a peripheral vascular disease,
wherein the treating comprises care, relief, attenuation or arrest of progression of the damaged peripheral vascular wall,
wherein said 11-deoxy-prostaglandin compound is a compound represented by the following formula (III):

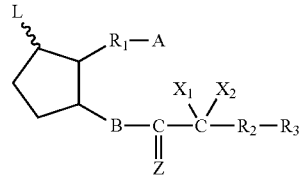

(III)

wherein L is hydrogen, hydroxy or oxo, wherein the five-membered ring may optionally have at least one double bond;
A is —$CH_3$, —$CH_2OH$, —$COCH_2OH$, —COOH or a salt, ether, ester or amide thereof;
B is —$CH_2$—$CH_2$—;
Z is

wherein $R_4$ and $R_5$ are hydrogen or hydroxy, wherein $R_4$ and $R_5$ are not hydroxy at the same time;
$X_1$ and $X_2$ are hydrogen or halogen;
$R_1$ is a saturated or unsaturated bivalent lower or medium aliphatic hydrocarbon;

$R_2$ is a single bond or lower alkylene; and
$R_3$ is lower alkyl.

12. A method for treating damaged peripheral vascular endothelial cells in a mammalian subject, which comprises administering an effective amount of an 11-deoxy-prostaglandin compound to the subject in need of treatment of a peripheral vascular disease,
wherein the treating comprises care, relief, attenuation or arrest of progression of the damaged peripheral vascular endothelial cells,
wherein said 11-deoxy-prostaglandin compound is a compound represented by the following formula (III):

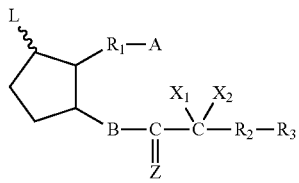

(III)

wherein L is hydrogen, hydroxy or oxo, wherein the five-membered ring may optionally have at least one double bond;
A is $-CH_3$, $-CH_2OH$, $-COCH_2OH$, $-COOH$ or a salt, ether, ester or amide thereof;
B is $-CH_2-CH_2-$;
Z is

wherein $R_4$ and $R_5$ are hydrogen or hydroxy, wherein $R_4$ and $R_5$ are not hydroxy at the same time;
$X_1$ and $X_2$ are hydrogen or halogen;
$R_1$ is a saturated or unsaturated bivalent lower or medium aliphatic hydrocarbon;
$R_2$ is a single bond or lower alkylene; and
$R_3$ is lower alkyl.

13. A method for increasing cutaneous tissue blood flow in a mammalian subject, which comprises administering an effective amount of an 11-deoxy-prostaglandin compound to the subject in need of treatment of a peripheral vascular disease,
wherein said 11-deoxy-prostaglandin compound is a compound represented by the following formula (III):

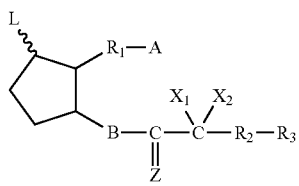

(III)

wherein L is hydrogen, hydroxy or oxo, wherein the five-membered ring may optionally have at least one double bond;
A is $-CH_3$, $-CH_2OH$, $-COCH_2OH$, $-COOH$ or a salt, ether, ester or amide thereof;
B is $-CH_2-CH_2-$;
Z is

wherein $R_4$ and $R_5$ are hydrogen or hydroxy, wherein $R_4$ and $R_5$ are not hydroxy at the same time;
$X_1$ and $X_2$ are hydrogen or halogen;
$R_1$ is a saturated or unsaturated bivalent lower or medium aliphatic hydrocarbon;
$R_2$ is a single bond or lower alkylene; and
$R_3$ is lower alkyl.

14. The method as described in claim 1, wherein at least one of $X_1$ and $X_2$ is a halogen atom.

15. The method as described in claim 11, wherein at least one of $X_1$ and $X_2$ is a halogen atom.

16. The method as described in claim 12, wherein at least one of $X_1$ and $X_2$ is a halogen atom.

17. The method as described in claim 13, wherein at least one of $X_1$ and $X_2$ is a halogen atom.

18. The method as described in claim 11, wherein said 11-deoxy-prostaglandin compound is an 11-deoxy-13,14-dihydro-15-keto-prostaglandin compound.

19. The method as described in claim 11, wherein said 11-deoxy-prostaglandin compound is an 11-deoxy-13,14-dihydro-16-mono or dihalogen-prostaglandin compound.

20. The method as described in claim 11, wherein said 11-deoxy-prostaglandin compound is an 11-deoxy-13,14-dihydro-15-keto-16-mono or dihalogen-prostaglandin compound.

21. The method as described in claim 11, wherein said 11-deoxy-prostaglandin compound is an 11-deoxy-13,14-dihydro-15-keto-16-mono or difluoro-prostaglandin compound.

22. The method as described in claim 11, wherein said 11-deoxy-prostaglandin compound is an 11-deoxy-13,14-dihydro-15-keto-16-mono or dihalogen-prostaglandin E or F compound.

23. The method as described in claim 11, wherein said prostaglandin compound is an 11-deoxy-13,14-dihydro-15-keto-16-mono or difluoro-prostaglandin E or F compound.

24. The method as described in claim 11, wherein said prostaglandin compound is an 11-deoxy-13,14-dihydro-15-keto-16,16-difluoro-prostaglandin $E_1$ compound.

25. The method as described in claim 12, wherein said 11-deoxy-prostaglandin compound is an 11-deoxy-13,14-dihydro-15-keto-prostaglandin compound.

26. The method as described in claim 12, wherein said 11-deoxy-prostaglandin compound is an 11-deoxy-13,14-dihydro-16-mono or dihalogen-prostaglandin compound.

27. The method as described in claim 12, wherein said 11-deoxy-prostaglandin compound is an 11-deoxy-13,14-dihydro-15-keto-16-mono or dihalogen-prostaglandin compound.

28. The method as described in claim 12, wherein said 11-deoxy-prostaglandin compound is an 11-deoxy-13,14-dihydro-15-keto-16-mono or difluoro-prostaglandin compound.

29. The method as described in claim 12, wherein said 11-deoxy-pro staglandin compound is an 11-deoxy-13,14-dihydro-15-keto-16-mono or dihalogen-prostaglandin E or F compound.

30. The method as described in claim 12, wherein said prostaglandin compound is an 11-deoxy-13,14-dihydro-15-keto-16-mono or difluoro-prostaglandin E or F compound.

31. The method as described in claim 12, wherein said prostaglandin compound is an 11-deoxy-13,14-dihydro-15-keto-16,16-difluoro-prostaglandin $E_1$ compound.

32. The method as described in claim 13, wherein said 11-deoxy-prostaglandin compound is an 11-deoxy-13,14-dihydro-15-keto-prostaglandin compound.

33. The method as described in claim 13, wherein said 11-deoxy-prostaglandin compound is an 11-deoxy-13,14-dihydro-16-mono or dihalogen-prostaglandin compound.

34. The method as described in claim 13, wherein said 11-deoxy-prostaglandin compound is an 11-deoxy-13,14-dihydro-15-keto-16-mono or dihalogen-prostaglandin compound.

35. The method as described in claim 13, wherein said 11-deoxy-prostaglandin compound is an 11-deoxy-13,14-dihydro-15-keto-16-mono or difluoro-prostaglandin compound.

36. The method as described in claim 13, wherein said 11-deoxy-prostaglandin compound is an 11-deoxy-13,14-dihydro-15-keto-16-mono or dihalogen-prostaglandin E or F compound.

37. The method as described in claim 13, wherein said prostaglandin compound is an 11-deoxy-13,14-dihydro-15-keto-16-mono or difluoro-prostaglandin E or F compound.

38. The method as described in claim 13, wherein said prostaglandin compound is an 11-deoxy-13,14-dihydro-15-keto-16,16-difluoro-prostaglandin $E_1$ compound.

39. A method for treating a peripheral vascular disease in a mammalian subject, which comprises administering an effective amount of 11-deoxy-13,14-dihydro-15-keto-16,16-difluoro-$PGE_1$ or a salt, ester or amide thereof the subject in need of treatment of a peripheral vascular disease,
wherein the treating comprises care, relief, attenuation or arrest of progression of the peripheral vascular disease.

40. A method for treating damaged peripheral vascular wall in a mammalian subject, which comprises administering an effective amount of 11-deoxy-13,14-dihydro-15-keto-16,16-difluoro-$PGE_1$ or a salt, ester or amide thereof to the subject in need of treatment of damaged peripheral vascular wall,
wherein the treating comprises care, relief, attenuation or arrest of progression of the damaged peripheral vascular wall.

41. A method for treating damaged peripheral vascular endothelial cells in a mammalian subject, which comprises administering an effective amount of 11-deoxy-13,14-dihydro-15-keto-16,16-difluoro-$PGE_1$ or a salt, ester or amide thereof to the subject in need of treatment of damaged peripheral vascular endothelial cells,
wherein the treating comprises care, relief, attenuation or arrest of progression of the damaged peripheral vascular endothenlial cells.

42. A method for increasing cutaneous tissue blood flow in a mammalian subject, which comprises administering an effective amount of 11-deoxy-13,14-dihydro-15-keto-16,16-difluoro-$PGE_1$ or a salt, ester or amide thereof to the subject in need of increased cutaneous tissue blood flow.

43. The method as described in claim 39, wherein said prostaglandin compound is 11-deoxy-13,14-dihydro-15-keto-16,16-difluoro-prostaglandin $E_1$.

44. The method as described in claim 40, wherein said prostaglandin compound is 11-deoxy-13,14-dihydro-15-keto-16,16-difluoro-prostaglandin $E_1$.

45. The method as described in claim 41, wherein said prostaglandin compound is 11-deoxy-13,14-dihydro-15-keto-16,16-difluoro-prostaglandin $E_1$.

46. The method as described in claim 42, wherein said prostaglandin compound is 11-deoxy-13,14-dihydro-15-keto-16,16-difluoro-prostaglandin $E_1$.

47. The method according to claim 1, wherein the 11-deoxy-prostaglandin compound is selected from the group consisting of:
11-deoxy-13,14-dihydro-15-keto-16,16-difluoro-$PGE_1$,
11-deoxy-13,14-dihydro-16,16-difluoro-$PGE_1$,
11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$,
11-deoxy-13,14-dihydro-15-keto-16,16-difluoro-20-methyl-$PGE_1$ isopropyl ester,
11-deoxy-13,14-dihydro-15-keto-16,16-difluoro-20-methyl-$PGE_1$,
11-deoxy-13,14-dihydro-15-keto-16,16-difluoro-20-ethyl-$PGE_1$,
11-deoxy-13,14-dihydro-15-keto-16,16-difluoro-$PGE_1$ methyl ester,
11-deoxy-13,14-dihydro-15-keto-16,16-difluoro-20-ethyl-$PGE_1$ isopropyl ester, and
11-deoxy-13,14-dihydro-15-keto-16,16-difluoro-$PGF_{1\alpha}$ isopropyl ester.

48. The method according to claim 11, wherein the 11-deoxy-prostaglandin compound is selected from the group consisting of:
11-deoxy-13,14-dihydro-15-keto-16,16-difluoro-$PGE_1$,
11-deoxy-13,14-dihydro-16,16-difluoro-$PGE_1$,
11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$,
11-deoxy-13,14-dihydro-15-keto-16,16-difluoro-20-methyl-$PGE_1$ isopropyl ester,
11-deoxy-13,14-dihydro-15-keto-16,16-difluoro-20-methyl-$PGE_1$,
11-deoxy-13,14-dihydro-15-keto-16,16-difluoro-20-ethyl-$PGE_1$,
11-deoxy-13,14-dihydro-15-keto-16,16-difluoro-$PGE_1$ methyl ester,
11-deoxy-13,14-dihydro-15-keto-16,16-difluoro-20-ethyl-$PGE_1$ isopropyl ester, and
11-deoxy-13,14-dihydro-15-keto-16,16-difluoro-$PGF_{1\alpha}$ isopropyl ester.

49. The method according to claim 12, wherein the 11-deoxy-prostaglandin compound is selected from the group consisting of:
11-deoxy-13,14-dihydro-15-keto-16,16-difluoro-$PGE_1$,
11-deoxy-13,14-dihydro-16,16-difluoro-$PGE_1$,
11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$ isopropyl ester,
2-decarboxy-2-(2-carboxyethyl)-11-deoxy-13,14-dihydro-15-keto-16,16-difluoro-$PGE_1$,
11-deoxy-13,14-dihydro-15-keto-16,16-difluoro-20-methyl-$PGE_1$ isopropyl ester,
11-deoxy-13,14-dihydro-15-keto-16,16-difluoro-20-methyl-$PGE_1$,
11-deoxy-13,14-dihydro-15-keto-16,16-difluoro-20-ethyl-$PGE_1$, 11-deoxy-13,14-dihydro-15-keto-16,16-difluoro-PGE$_1$ methyl ester,
11-deoxy-13,14-dihydro-15-keto-16,16-difluoro-20-ethyl-PGE$_1$ isopropyl ester, and
11-deoxy-13,14-dihydro-15-keto-16,16-difluoro-PGF$_{1\alpha}$ isopropyl ester.

50. The method according to claim 13, wherein the 11-deoxy-prostaglandin compound is selected from the group consisting of:
11-deoxy-13,14-dihydro-15-keto-16,16-difluoro-PGE$_1$,
11-deoxy-13,14-dihydro-16,16-difluoro-PGE$_1$,
11-deoxy-13,14-dihydro-15-keto-16,16-difluoro-PGE$_1$ isopropyl ester,
2-decarboxy-2-(2-carboxyethyl)-11-deoxy-13,14-dihydro-15-keto-16,16-difluoro-PGE$_1$ isopropyl ester,
2-decarboxy-2-(2-carboxyethyl)-11-deoxy-13,14-dihydro-15-keto-16,16-difluoro-PGE$_1$,
11-deoxy-13,14-dihydro-15-keto-16,16-difluoro-20-methyl-PGE$_1$ isopropyl ester,
11-deoxy-13,14-dihydro-15-keto-16,16-difluoro-20-methyl-PGE$_1$,
11-deoxy-13,14-dihydro-15-keto-16,16-difluoro-20-ethyl-PGE$_1$,
11-deoxy-13,14-dihydro-15-keto-16,16-difluoro-PGE$_1$ methyl ester,
11-deoxy-13,14-dihydro-15-keto-16,16-difluoro-20-ethyl-PGE$_1$ isopropyl ester, and
11-deoxy-13,14-dihydro-15-keto-16,16-difluoro-PGF$_{1\alpha}$ isopropyl ester.

* * * * *